United States Patent
Gotfried

(10) Patent No.: US 7,763,023 B2
(45) Date of Patent: Jul. 27, 2010

(54) INTRAMEDULLARY NAIL SYSTEM AND METHOD FOR FIXATION OF A FRACTURED BONE

(76) Inventor: Yechiel Gotfried, 16 ushe str., Kiryat-Motzkin 28364 (IL)

( * ) Notice: Subject to any disclaimer, the term of this patent is extended or adjusted under 35 U.S.C. 154(b) by 480 days.

(21) Appl. No.: 11/704,862

(22) Filed: Feb. 9, 2007

(65) Prior Publication Data
US 2008/0195098 A1    Aug. 14, 2008

(51) Int. Cl.
*A61B 17/56* (2006.01)
(52) U.S. Cl. .......................... 606/64; 606/62
(58) Field of Classification Search ............ 606/62–68, 606/96–98, 329; 623/23.23; 403/348–349
See application file for complete search history.

(56) References Cited

U.S. PATENT DOCUMENTS

| | | | |
|---|---|---|---|
| 3,019,789 A | | 2/1962 | Whitehill et al. |
| 3,433,220 A | | 3/1969 | Zickel |
| 4,176,815 A | * | 12/1979 | Davidson et al. ............ 403/349 |
| 4,522,202 A | | 6/1985 | Otte et al. |
| 4,827,917 A | | 5/1989 | Brumfield |
| 5,032,125 A | * | 7/1991 | Durham et al. ............... 606/62 |
| 5,066,296 A | | 11/1991 | Chapman et al. |
| 5,074,882 A | | 12/1991 | Grammont et al. |
| 5,122,141 A | | 6/1992 | Simpson et al. |
| 5,176,681 A | | 1/1993 | Lawes et al. |
| 5,178,621 A | | 1/1993 | Cook et al. |
| 5,334,192 A | | 8/1994 | Behrens |
| 5,403,321 A | | 4/1995 | DiMarco |
| 5,454,813 A | * | 10/1995 | Lawes ......................... 606/62 |
| 5,489,284 A | | 2/1996 | James et al. |
| 5,531,748 A | * | 7/1996 | de la Caffiniere ............ 606/62 |
| 5,653,709 A | | 8/1997 | Frigg |
| 5,658,287 A | | 8/1997 | Hofmann et al. |

(Continued)

FOREIGN PATENT DOCUMENTS

DE         2906068 A1      6/1980

(Continued)

OTHER PUBLICATIONS

U.S. Appl. No. 10/616,218, filed Jul. 8, 2003, Entitled "Intramedullary Nail System and Method for Fixation of a Fractured Bone", Inventor: Y. Gotfried.

(Continued)

*Primary Examiner*—Eduardo C Robert
*Assistant Examiner*—Steven J Cotroneo
(74) *Attorney, Agent, or Firm*—Frishauf, Holtz, Goodman & Chick, P.C.

(57) ABSTRACT

Apparatus for treating a fracture of a bone of a subject including an intramedullary (IM) elongate member insertable into a medullary canal of a first part of the bone of the subject, and having a proximal head defining at least one hole therethrough. A sleeve includes an engagement mechanism and is arranged to engage one of the at least one hole when the sleeve is within that hole. This engagement restricts rotational and longitudinal movement between the sleeve and the elongate member after the sleeve is engaged with that hole. A screw or pin is movably arranged inside the sleeve for securing a second part of the bone to the first part of the bone, i.e., the part into which the elongate member is inserted.

16 Claims, 17 Drawing Sheets

U.S. PATENT DOCUMENTS

| | | | |
|---|---|---|---|
| 5,662,652 | A | 9/1997 | Schafer et al. |
| 5,728,128 | A | 3/1998 | Crickenberger et al. |
| 5,915,482 | A * | 6/1999 | Carruthers ............... 403/348 |
| 6,139,550 | A | 10/2000 | Michelson |
| 6,183,477 | B1 | 2/2001 | Pepper |
| 6,235,031 | B1 | 5/2001 | Hodgeman et al. |
| 6,270,499 | B1 | 8/2001 | Leu et al. |
| 6,331,179 | B1 | 12/2001 | Freid et al. |
| 6,443,954 | B1 | 9/2002 | Bramlet et al. |
| 6,494,636 | B1 * | 12/2002 | Mozena ............... 403/349 |
| 6,565,573 | B1 | 5/2003 | Ferrante et al. |
| 6,569,165 | B2 | 5/2003 | Wahl et al. |
| 6,648,889 | B2 | 11/2003 | Bramlet et al. |
| 6,656,189 | B1 | 12/2003 | Wilson et al. |
| 7,147,399 | B2 | 12/2006 | Viscount et al. |
| 7,455,673 | B2 * | 11/2008 | Gotfried ............... 606/62 |
| 7,488,328 | B2 | 2/2009 | Gotfried |
| 7,608,075 | B2 | 10/2009 | Tornier |
| 2002/0151898 | A1 | 10/2002 | Sohngen et al. |
| 2002/0156473 | A1 * | 10/2002 | Bramlet et al. ............ 606/62 |
| 2003/0231927 | A1 * | 12/2003 | Hale ............... 403/349 |
| 2004/0122431 | A1 | 6/2004 | Biedermann et al. |
| 2005/0010223 | A1 * | 1/2005 | Gotfried ............... 606/62 |
| 2005/0055023 | A1 | 3/2005 | Sohngen et al. |
| 2006/0100626 | A1 | 5/2006 | Rathbun et al. |
| 2006/0241606 | A1 * | 10/2006 | Vachtenberg et al. ........ 606/65 |
| 2007/0049939 | A1 | 3/2007 | Wallace et al. |
| 2008/0058813 | A1 | 3/2008 | Gotfried |
| 2008/0058814 | A1 | 3/2008 | Gotfried |
| 2008/0119856 | A1 | 5/2008 | Gotfried |

FOREIGN PATENT DOCUMENTS

| | | |
|---|---|---|
| DE | 8701164 U1 | 7/1987 |
| EP | 0 257 118 A1 | 3/1988 |
| EP | 0321170 A1 | 6/1989 |
| EP | 0441577 A2 | 8/1991 |
| EP | 0 521 600 A1 | 1/1993 |
| WO | WO 02/083015 A1 | 10/2002 |
| WO | WO2004110292 * | 12/2004 |

OTHER PUBLICATIONS

U.S. Appl. No. 11/932,665, filed Oct. 31, 2007; Entitled "Apparatus for Treating a Fractured Bone", Inventor: Y. Gotfried.

U.S. Appl. No. 11/932,719, filed Oct. 31, 2007; Entitled "Apparatus for Treating a Fractured Bone", Inventor: Y. Gotfried.

U.S. Appl. No. 10/896,125, filed Jul. 20, 2004, Entitled "Targeting Apparatus for Bone Fixation Device", Inventor: Y. Gotfried.

U.S. Appl. No. 11/601,906, filed Nov. 20, 2006, Entitled "Intramedullary nail system and method for fixation of a fractured bone", Inventor: Y. Gotfried.

Office Action dated Apr. 19, 2010 issued in related U.S. Appl. No. 11/601,906.

* cited by examiner

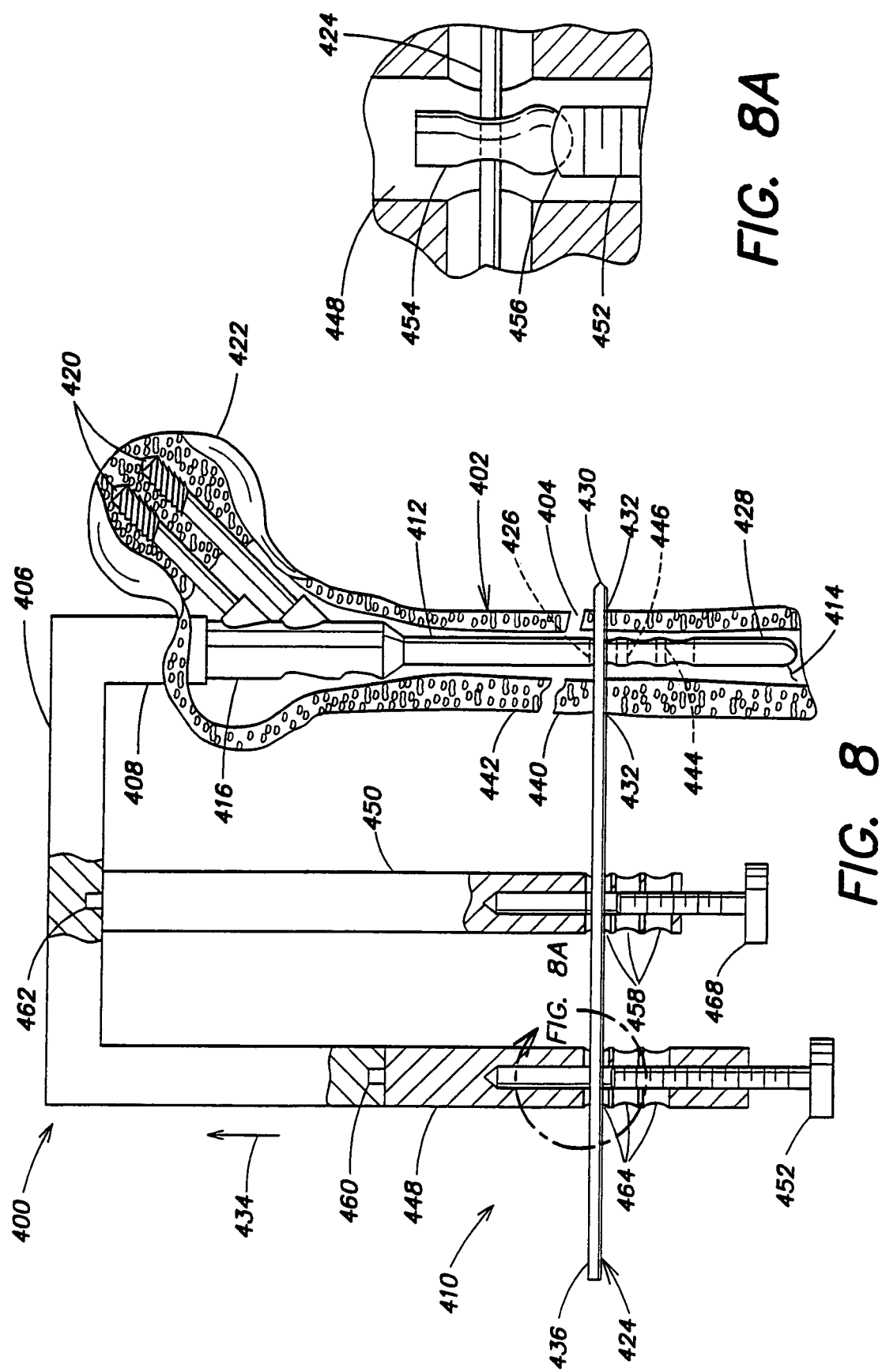

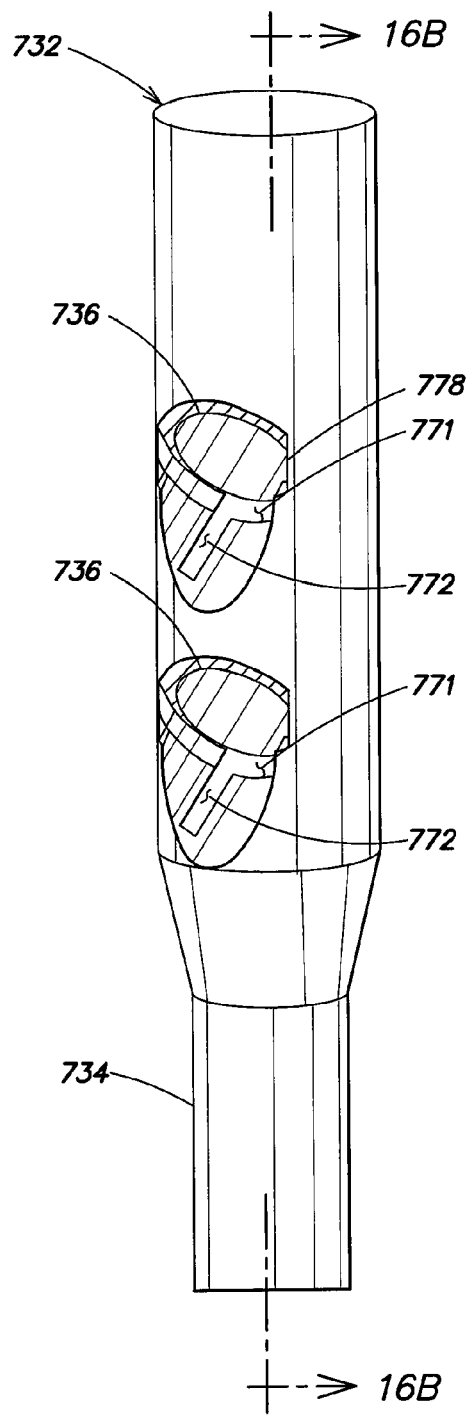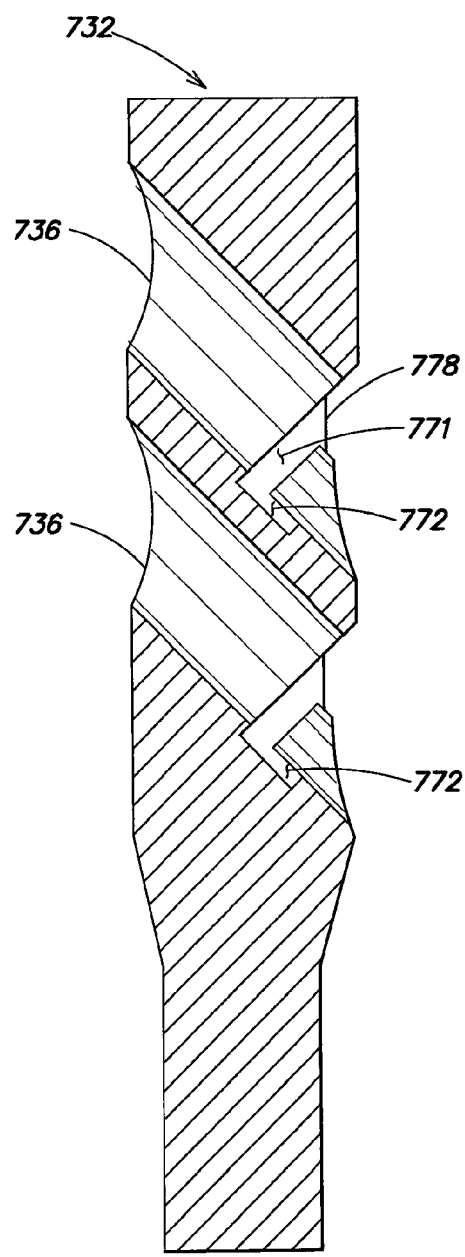
FIG. 16A
FIG. 16B

INTRAMEDULLARY NAIL SYSTEM AND METHOD FOR FIXATION OF A FRACTURED BONE

RELATED APPLICATIONS

This application is related to U.S. patent application Ser. No. 10/616,218, filed Jul. 8, 2003 and U.S. patent application Ser. No. 11/601,906 filed Nov. 20, 2006, the entire contents of which are incorporated by reference herein.

BACKGROUND OF THE INVENTION

Intramedullary (IM) nails are implantable devices used to stabilize fractures and allow for bone healing. IM nails are inserted into the medullary canal of the long bones of the extremities, e.g., the femur or tibia. Currently-used IM nails have a head region that generally includes at least one hole, transverse to the longitudinal axis of the nail, for receiving anchoring means, such as a screw, to secure the nail within the medullary canal of the bone. Some such anchoring means include at least one sleeve, which passes through the transverse hole, and through which a screw assembly typically passes freely. A proximal end of the head region protrudes from the proximal end of the bone, to facilitate post-implantation access to the IM nail, if desired. The proximal end of the head region, which protrudes from the bone, is a continuous extension of the head region, not structurally or visually distinct from the more distal portion of the head region that includes the holes.

U.S. Patent Application Publication No. 2005/0010223 to Gotfried, which is incorporated herein by reference, describes apparatus for treating a fracture of a bone of a subject. The apparatus includes an intramedullary (IM) nail, adapted to be inserted in a medullary canal of the bone of the subject. The IM nail has a proximal head that defines at least one hole therethrough. The apparatus also includes a sleeve, which includes a locking mechanism, which locking mechanism is adapted to engage the hole when the sleeve is inserted in the hole, such engagement preventing rotational and longitudinal movement between the sleeve and the hole. In an embodiment, the apparatus includes a screw, the sleeve being adapted to slidably receive the screw.

U.S. Pat. No. 4,827,917 to Brumfield, which is incorporated herein by reference, describes an IM system including a screw and an intramedullary rod. The screw has a threaded portion and a smooth portion, and the rod has a head, stem and a longitudinal bore. There is at least one pair of coaxial holes through the stem, transverse to the longitudinal axis of the rod, for receiving first anchoring means, such as a nail, screw or bolt, to secure the rod within the marrow canal of the femur. There are at least a proximal pair of coaxial holes and a distal pair of coaxial holes in the head of the rod in an angled direction toward the femoral head relative to the longitudinal axis of the rod. The distal pair of head holes are adapted to slidingly receive the screw so as to permit the threaded portion of the screw, in use, to engage the femoral head and to allow sliding compression of a femoral neck or intertrochanteric fracture.

U.S. Pat. No. 5,032,125 to Durham et al., which is incorporated herein by reference, describes an IM hip screw that includes an IM rod, a lag screw and a sleeve for slidably receiving the lag screw. The sleeve is received in a passage in the IM rod having an axis positioned at an angle relative to the longitudinal axis of the IM rod such that the axis of the sleeve is directed toward the head of the femur. The IM hip screw is described as permitting sliding compression of selected fractures, particularly intertrochanteric fractures and fractures of the femoral neck.

U.S. Pat. No. 6,443,954 to Bramlet et al., which is incorporated herein by reference, describes an IM system that includes a lag screw assembly extending through a radial bore in an IM nail. The lag screw is inserted into one portion of a bone and deployed to fix the leading end. The IM nail is placed in the IM canal of a portion of the bone and the trailing end of the lag screw assembly is adjustably fixed in the radial bore to provide compression between the lag screw assembly and the IM nail. The IM nail has a cap screw in the proximal end holding the lag screw assembly and a tang in the distal end. The tang has legs extending through the nail to fix the distal end in the IM canal.

U.S. Pat. No. 6,235,031 to Hodgeman et al., which is incorporated herein by reference, describes an IM system that includes an IM rod, a lag screw, and a lag screw collar. The rod has a proximal end with a transverse bore extending therethrough. The lag screw has a distal end with coarse bone engaging thread elements and a proximal end with screw threads. When in use, the lag screw is substantially axially aligned with the transverse bore of the rod. The lag screw collar has an outer diameter sized to rotatably fit within the transverse bore of the rod. The collar also has an inner diameter and internal screw threads adapted to cooperate with the screw threads of the proximal end of the lag screw. The lag screw collar may have an increased outer diameter at one end thereof which is at least slightly larger than a diameter of the transverse bore of the rod.

U.S. Patent Application Publication No. 2002/0151898 to Sohngen et al., which is incorporated herein by reference, describes an IM nail having a modular configuration, including a nail member having a chamber formed on the proximal end thereof. An insert having at least one opening therein for receiving a bone screw or fastener is disposed within the chamber and is secured therein by a locking ring. Various inserts are described for use to achieve selected bone screw or fastener configurations.

U.S. Patent Application Publication No. 2002/0156473 to Bramlet et al., which is incorporated herein by reference, describes an IM system that includes an IM nail for insertion in the femur. The nail has an axial bore and an intersecting transverse bore. A lag screw is inserted through the transverse bore and turned into the head of the femur. A slotted sleeve is inserted over the lag screw and through the transverse bore with the slots aligned with the axial bore. A sleeve lock is inserted into the axial bore, and has a locking tab which engages the slots in the sleeve preventing rotational and longitudinal movement between the sleeve and the nail. A compression screw is turned into the trailing end of the lag screw and engages the encircling sleeve to provide longitudinal translation between the lag screw and sleeve to apply compressive force across a fracture.

European Patent Application Publication No. EP 0 521 600 to Lawes, which is incorporated herein by reference, describes an IM system that includes an IM rod having an angulated opening to receive a femoral neck screw having a threaded portion at its distal end, and locking means acting between the neck screw and the wall of the angulated opening to prevent relative rotation between the screw and the rod.

PCT Publication WO 02/083015 to Ferrante et al., which is incorporated herein by reference, describes an orthopedic screw having a screw head, a screw body with a distal tip, a shank with an enlarged diameter at the trailing end and a thread extending radially outward from the shank, and an internal capture surface. The screw is used with an orthopedic implant system, which includes an orthopedic implant and a driver capable of engaging the internal capture of the screw.

The following references, which are incorporated by reference herein, may be of interest:

U.S. Pat. No. 6,648,889 to Bramlet et al
U.S. Pat. No. 5,454,813 to Lawes
U.S. Pat. No. 3,433,220 to Zickel
EP A 0 321 170 Howemedica
DE U 8 701 164 Howemedica
DE A 2 906 068 Synthes AG
EP A 0 441 577 Smith & Nephew Richards

SUMMARY OF THE INVENTION

In some embodiments of the present invention, an intramedullary (IM) system for implantation in a medullary canal of a femur of a subject comprises an IM nail having a head and a stem. The head of the IM nail defines at least one hole, which is oriented in an angled direction toward the femoral head relative to the longitudinal axis of the IM nail. The head hole is adapted to receive a sleeve, which is adapted to slidably receive a screw, so as to permit a threaded portion of the screw to engage a femoral head of the subject and to allow sliding compression of a femoral neck or intertrochanteric fracture. The sleeve comprises an engagement mechanism, which engages the head hole, restricting longitudinal and rotational movement of the sleeve with respect to the head hole after being inserted.

Typically, but not necessarily, the engagement mechanism inhibits longitudinal movement of the sleeve with respect to the head hole in only one direction (e.g., by inhibiting downward or upward motion of the sleeve depending on the direction of implantation of the arrangement), but the IM nail may be formed such that the longitudinal restriction and a rotational restriction form a total restriction unless subjected to releasing maneuvers.

For some applications, the engagement mechanism allows rotation of the sleeve with respect to the head hole in one direction, e.g., only one direction. Alternatively, substantially no rotation is possible once the engagement mechanism has engaged the IM nail, unless preceded by longitudinal movement.

For some applications, the engagement mechanism of the sleeve engages the head hole by providing rotation of the sleeve within the head hole, followed by inferior-medial, longitudinal motion of the sleeve within the head hole to complete the engagement. Subsequently, if desired, the engagement provided by the engagement mechanism may be released by reversing these steps (i.e., moving the sleeve in a superior-lateral direction, and then rotating the sleeve in a direction opposite to the previous rotation). In one embodiment, directions other than those specified herein are utilized.

In some embodiments of the present invention, an intramedullary (IM) system for implantation in a medullary canal of a femur of a subject, comprises an IM nail having a head and a stem. The head of the IM nail defines at least one hole, which is oriented in an angled direction toward the femoral head relative to the longitudinal axis of the IM nail. The head hole is adapted to receive a sleeve, which is adapted to slidably receive a screw, so as to permit a threaded portion of the screw to engage a femoral head of the subject and to allow sliding compression of a femoral neck or intertrochanteric fracture. The sleeve comprises a locking mechanism, which engages the head hole, preventing rotational and longitudinal movement between the sleeve and the head hole. The locking mechanism typically comprises a depressible male coupling element, such as a tab, configured so that when the sleeve is inserted into the head hole and properly aligned, the tab engages a female coupling element, such as a notch, located on the inner surface of the head hole, thereby locking the sleeve to the head hole.

In some embodiments of the present invention, an IM system comprises an IM nail having a head and a stem. The head of the IM nail comprises a distal portion, which typically includes at least one head hole, and a proximal portion, having a diameter less than a diameter of the distal portion. For some applications, the diameter of the proximal portion is less than about 50% of the diameter of the distal portion. Such a narrower proximal portion typically allows greater regrowth and healing of the neck of the femur towards the area of the greater trochanter, than generally occurs upon implantation of conventional IM nail heads. At the same time, because a proximal end of the narrower proximal portion generally remains easily locatable on the external surface of the femur in the area of the tip of the greater trochanter or the piriformis, a surgeon typically can readily locate the IM nail if postoperative access to the implant becomes necessary. For some applications, the IM system further comprises the sleeve locking mechanism described hereinabove.

In some embodiments of the present invention, an IM locating tool is provided for locating an IM nail, a proximal portion of which does not extend to the surface of the femur. Without the use of this IM locating tool, it is sometimes difficult for a surgeon to locate such an IM nail if postoperative access to the implant becomes necessary. To use the locating tool, the surgeon temporarily couples one or more connecting elements of the locating tool to respective head holes of the IM nail. As a result, a proximal end of the locating tool is positioned directly over the site on the surface of the femur at which the surgeon should drill.

It is noted that use of the term "head" with respect to the IM nail is intended to distinguish at least a portion of the proximal end of the nail from the stem of the nail. In some embodiments, the head is separated by a neck region from the stem, while in other embodiments, the head and stem are generally continuous.

There is therefore provided, in accordance with an embodiment of the invention, apparatus for treating a fracture of a bone of a subject, including an intramedullary (IM) nail, configured to be inserted in a medullary canal of the bone of the subject, and including a proximal head that is shaped to define at least one hole therethrough; and a sleeve, including an engagement mechanism, which is configured to engage the hole when the sleeve is within the hole, such engagement restricting rotational and longitudinal movement between the sleeve and the hole after being engaged.

In one embodiment, the engagement mechanism includes a tab or projection that protrudes from an outer surface of the sleeve.

In one embodiment, the engagement mechanism is not mounted on any depressible portion of the sleeve.

In one embodiment, the IM nail is formed such that the one direction is from superior-lateral to inferior-medial with respect to a body of the subject when the IM nail is within the medullary canal. For some applications, the engagement mechanism is configured to engage the hole such that the longitudinal movement is achievable, following the engagement, only after rotating the sleeve. For some applications, the engagement mechanism is configured to be released only by rotational and longitudinal disengagement maneuvers.

BRIEF DESCRIPTION OF THE DRAWINGS

The present invention will be more fully understood from the following detailed description of embodiments thereof, taken together with the drawings, in which:

FIG. 8 is a schematic illustration of an introducer applied to a femur, in accordance with an embodiment of the present invention;

FIG. 16A is a schematic illustration of the head of the IM nail of FIG. 1, and FIG. 16B is a cross-sectional illustration of the head through the line A-A of FIG. 16A, in accordance with another embodiment of the present invention;

DETAILED DESCRIPTION OF THE INVENTION

Figure 1:
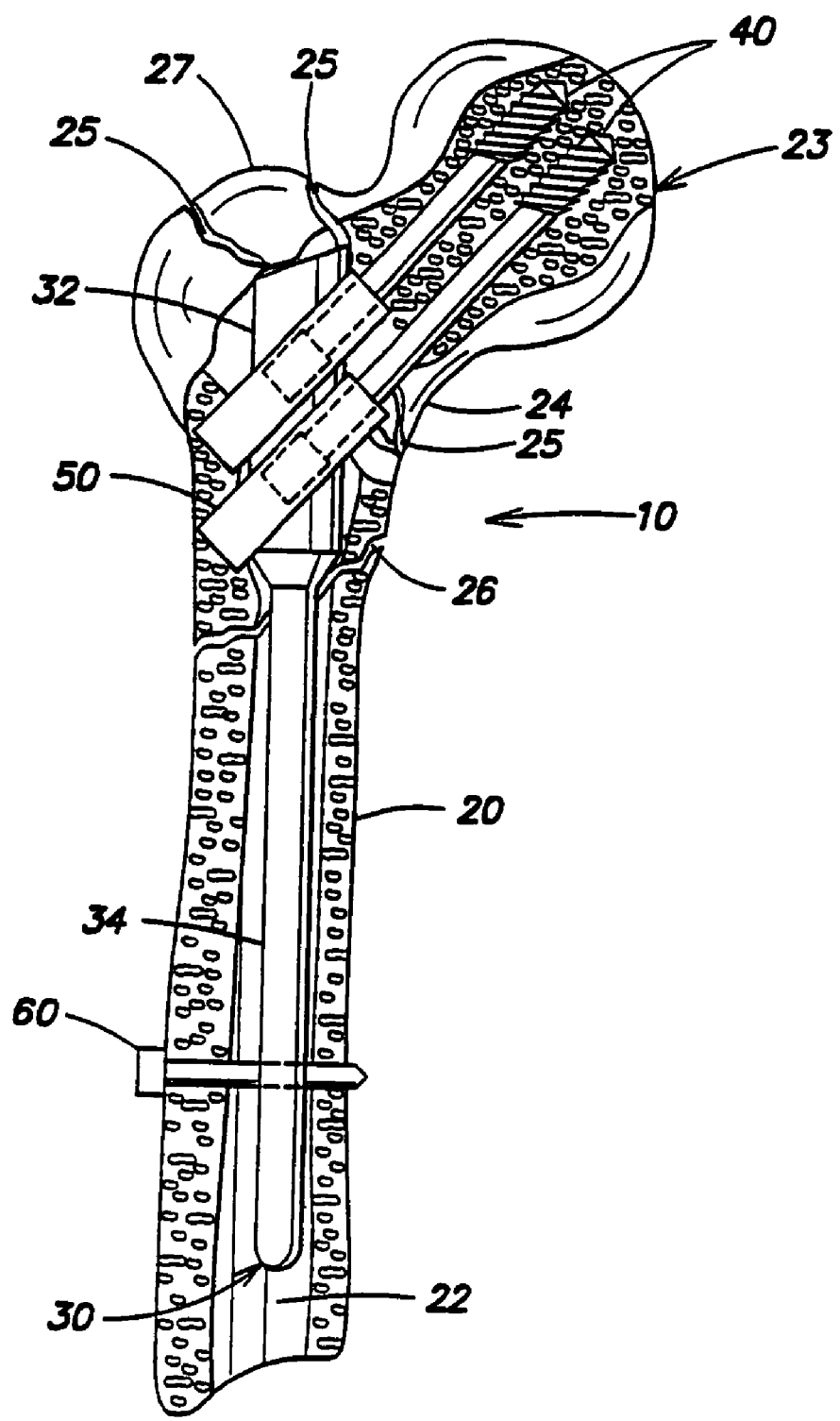
FIG. 1 is a schematic illustration of an intramedullary (IM) system in place in a femur, in accordance with an embodiment of the present invention.

FIG. 1 is a schematic illustration of an intramedullary (IM) system 10 in place in a femur 20, in accordance with an embodiment of the present invention. The IM system comprises an IM nail 30, having a proximal head 32 and a stem 34; at least one screw 40 for securing the IM nail at the head within a femoral head 23 of femur 20; and at least one sleeve 50. Alternatively, another anchoring element, such as a nail or bolt is used, instead of screw 40. IM system 10 typically further comprises at least one distal anchoring element 60, such as a screw, nail, or bolt, to secure IM nail 30 at stem 34 within a canal 22 of femur 20. For some applications, head 32 and/or stem 34 define a longitudinal bore (not shown).

Figure 2A:
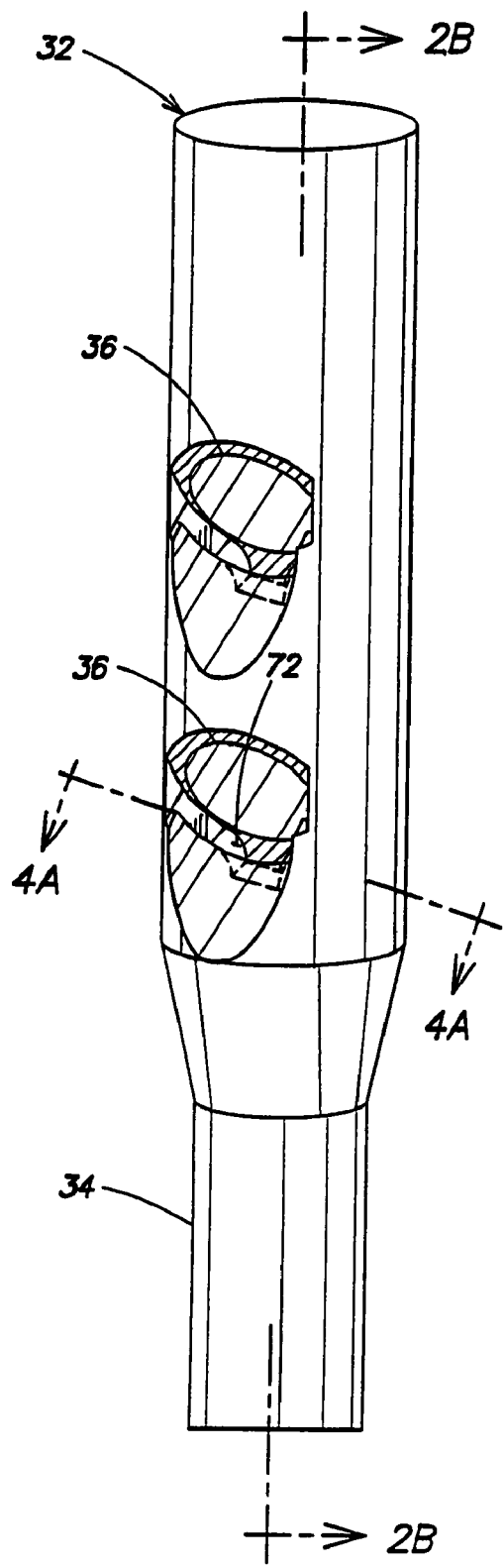
FIG. 2A is a schematic illustration of a head of the IM nail of FIG. 1.
Figure 2B:
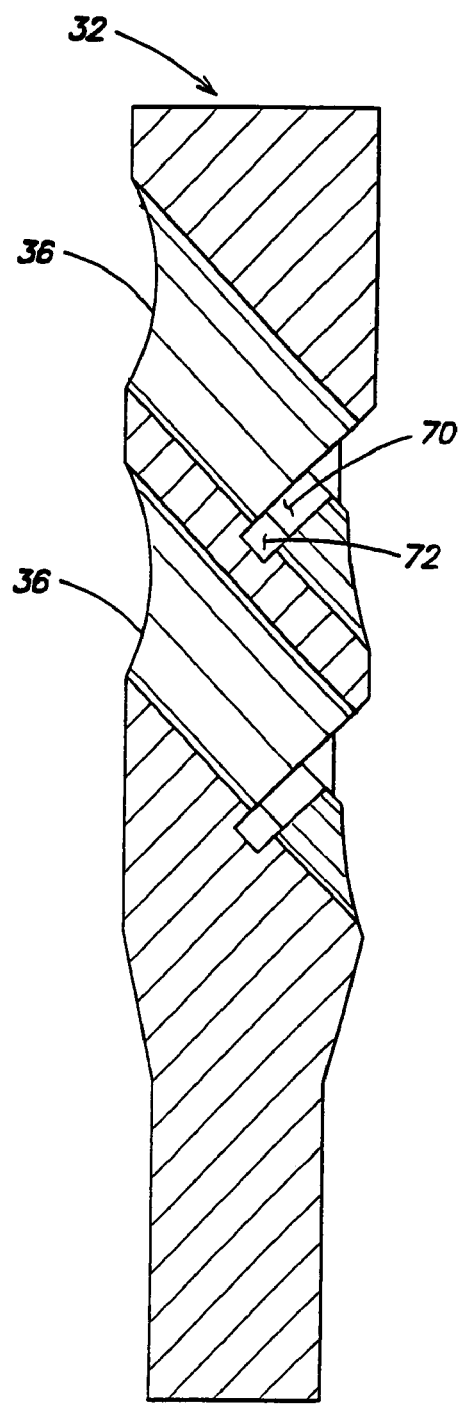
FIG. 2B is a cross-sectional illustration of the head through the line A-A of FIG. 2A, in accordance with an embodiment of the present invention.

Reference is now made to FIGS. 2A and 2B. FIG. 2A is a schematic illustration of head 32 of IM nail 30, and FIG. 2B is a cross-sectional illustration of head 32 through the line A-A of FIG. 2A, in accordance with an embodiment of the present invention. Head 32 defines at least one hole 36, typically two holes, as shown in the figures. Holes 36 are typically oriented in an angled direction toward a femoral head 23 (FIG. 1) relative to a longitudinal axis of IM nail 30.

Reference is again made to FIG. 1. In an embodiment of the present invention, head holes 36 are adapted to receive respective sleeves 50, which in turn are adapted to slidably receive screws 40, so as to permit a threaded portion of the screws to engage femoral head 23 and to allow sliding compression of a femoral neck 24, an intertrochanteric fracture 25, and/or a subtrochanteric fracture 26.

Figure 3:
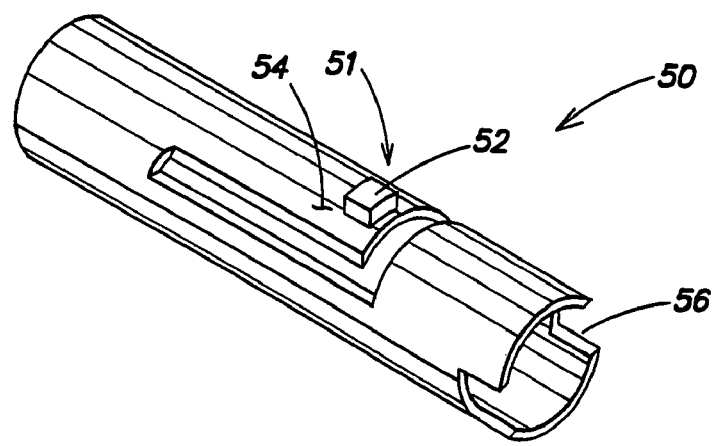
FIG. 3 is a schematic illustration of a sleeve for use with the IM system of FIG. 1, in accordance with an embodiment of the present invention.

FIG. 3 is a schematic illustration of sleeve 50, in accordance with an embodiment of the present invention. Sleeve 50 comprises a locking mechanism 51, which engages head hole 36, preventing rotational and longitudinal movement between sleeve 50 and head hole 36. The locking mechanism typically comprises a male coupling element, such as a tab 52 fixed to the outer surface of a depressible tongue 54, which is adapted to flex inwards toward the center of the sleeve when pressure is applied thereto. When the pressure is removed, tab 52 engages female coupling element, such as a notch 72 of hole 36, as described hereinbelow with reference to FIG. 4A. It is noted that in embodiments of the present invention, prevention of rotational and longitudinal movement between sleeve 50 and head hole 36 is not obtained by simply pressure-fitting the sleeve in the hole, or by simply screwing the sleeve in the hole, either of which generally would result in gradual loosening of the sleeve over time. In addition, sleeve 50 typically is shaped to define at least one cutout 56 to receive a screwdriver used by the surgeon to align the tab with the notch, as described hereinbelow with reference to FIGS. 4A and 4B.

Figure 4A:
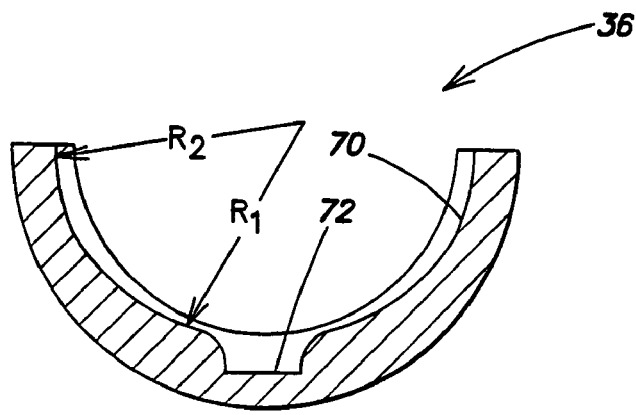
FIGS. 4A and 4B are cross-sectional illustrations of a head with one of the holes of FIG. 2A through the line B-B of FIG. 2A, in accordance with embodiments of the present invention.
Figure 4B:
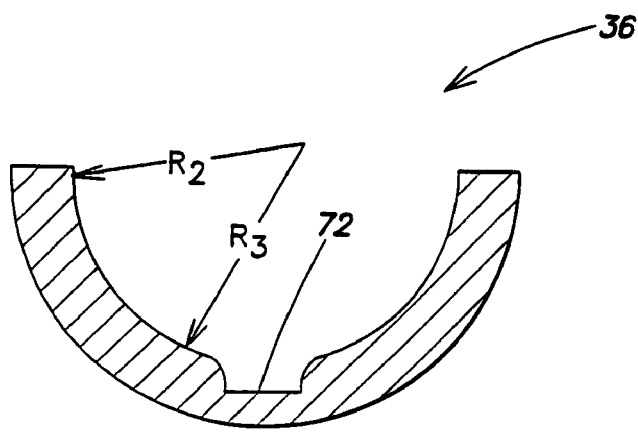

FIGS. 4A and 4B are cross-sectional illustrations of one of holes 36 of head 32 through the line B-B of FIG. 2A, in accordance with an embodiment of the present invention. An inner grooved surface 70 of hole 36 is shaped to define a notch 72, which tab 52 engages when sleeve 50 is inserted into hole 36 and properly aligned, thereby locking sleeve 50 to hole 36. In the embodiment shown in FIG. 4A, the radius $R_1$ of grooved inner surface 70 adjacent to notch 72 is less than the maximum radius $R_2$ of inner surface 70 in a region further away from notch 72. To insert sleeve 50 into hole 36 and engage locking mechanism 51, the surgeon typically first rotationally orients the sleeve so that tab 52 is aligned with a region of hole 36 having maximum radius $R_2$, for example at the upper portion of hole 36. The surgeon then inserts the sleeve in the hole until tab 52 of sleeve 50 meets the upper portion of hole 36, which blocks further insertion of the sleeve. The surgeon then rotates the sleeve so that tab 52 approaches notch 72. As tab 52 approaches notch 72, tab 52 (and tongue 54) is gradually depressed by inner surface 70, until the tab reaches the notch and the tongue springs back into its original position, forcing the tab into the notch, and locking it therein. Such a locking mechanism is generally impervious to loosening under cyclical loading, even over the course of many years. By contrast, two pieces which are attached without a locking mechanism (e.g., by being screwed together or wedged together) are susceptible to gradual loosening over time.

In the alternate embodiment shown in FIG. 4B, the radius $R_3$ of inner surface 70 adjacent to notch 72 is substantially equal to the maximum radius $R_2$ of inner surface 70. Hole 36 in this alternate embodiment is typically flared, such that the tab is depressed during insertion of sleeve 50 into hole 36. Insertion of sleeve 50 into hole 36 in this alternate embodiment does not necessarily include rotation of sleeve 50 (as is described with reference to FIG. 4A).

Figure 5A:
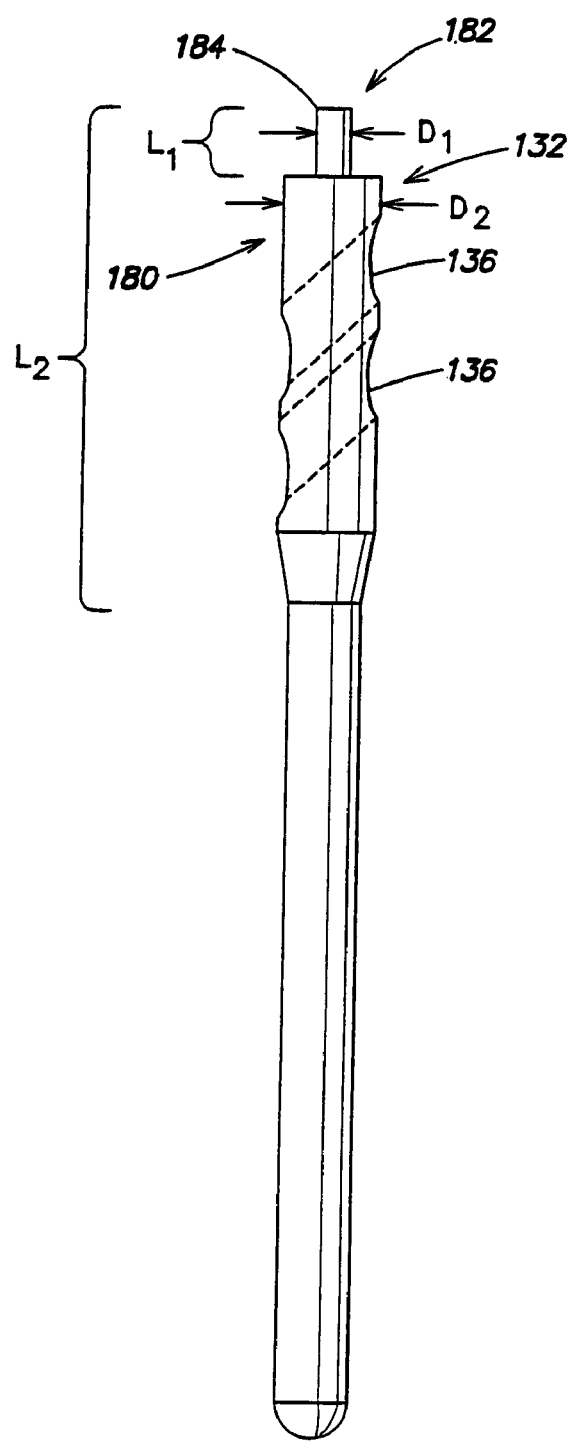
FIGS. 5A and 5B are schematic illustrations of a head of an IM nail, in accordance with embodiments of the present invention.

FIG. 5A is a schematic illustration of a head 132 of IM nail 30, in accordance with an embodiment of the present invention. In this embodiment, head 132 of IM nail 30 comprises a distal portion 180, which includes one or more head holes 136, and a proximal portion 182. Proximal portion 182 is adapted to aid in locating IM nail 30, while distal portion 180 is adapted to be coupled to at least one element, such as a nail, screw, or a sleeve. Proximal portion 182 is visually and structurally distinct from distal portion 180. Alternatively or additionally, proximal portion 182 has a diameter $D_1$ that is less than a diameter $D_2$ of distal portion 180 adjacent to proximal portion 182. For some applications, diameter $D_1$ is between 50% and about 80% of diameter $D_2$, or is less than about 50% of diameter $D_2$. For some applications, diameter $D_1$ is between about 25% and about 50% of diameter $D_2$. Typically, for IM nails intended for use in adults, diameter $D_1$ is between about 5 mm and about 10 mm, and diameter $D_2$ is between about 11 mm and about 17 mm. A length $L_1$ of proximal portion 182 is typically equal to between about 10% and about 50% of a length $L_2$ of head 132. For example, length $L_1$ may be between about 10 mm and about 35 mm, and length $L_2$ may be between about 40 mm and about 60 mm, in IM nails intended for use in adults. Although head 132 is shown in the figures as narrowing suddenly, for some applications the diameter of the head decreases gradually from $D_2$ to $D_1$. For some applications, such as for use in conjunction with the techniques described hereinbelow with reference to FIG. 6 or 7, (a) proximal portion 182 is removable, in which case the surgeon typically removes the proximal portion after implanting IM nail 30, or (b) head 132 does not comprise proximal portion 182, so that head 132 does not extend to the surface of femur 20.

Figure 5B:
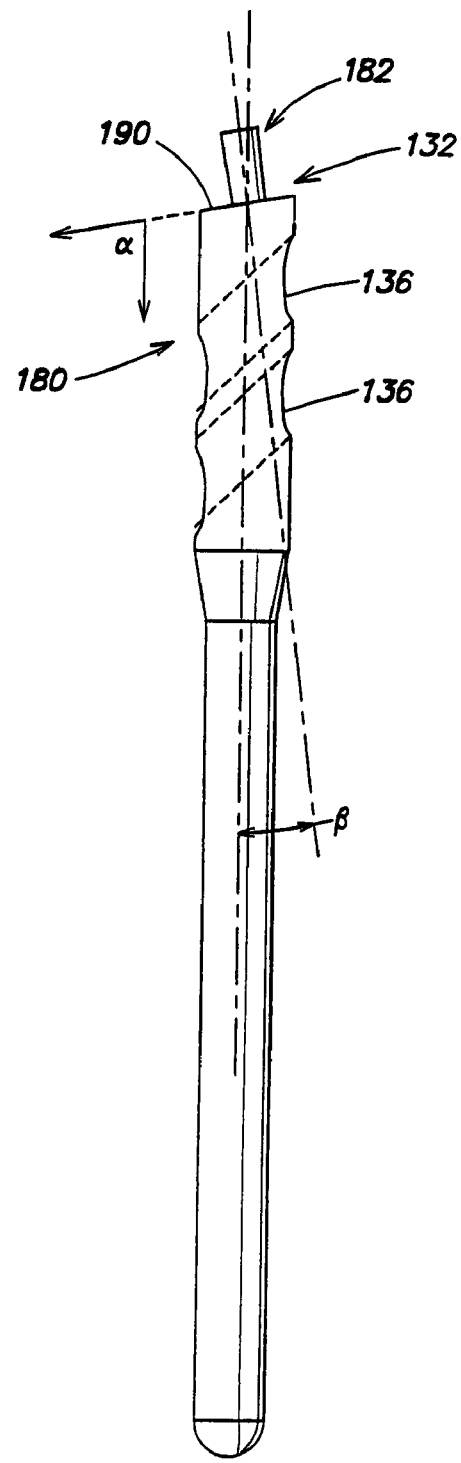

FIG. 5B is a schematic illustration of head 132 of IM nail 30, in accordance with an embodiment of the present invention. In this embodiment, a longitudinal axis of proximal portion 182 is oriented at an angle β with respect to a longitudinal axis of distal portion 180. Angle β is typically between about 4 and about 40 degrees, in this embodiment. Optionally, a proximal surface 190 of distal portion 180 is oriented at an angle α with respect to the longitudinal axis of distal portion 180. Angle α is typically between about 4 and about 40 degrees.

During an implantation procedure, IM nail 30 is typically inserted into femur 20 so that a proximal end 184 of proximal portion 182 is generally flush with or slightly protrudes from a surface region 27 of femur 20 in a vicinity of the greater trochanter or the piriformis (FIG. 1). As a result, a surgeon generally can readily locate the IM nail if post-operative access to the implant becomes necessary. In addition, such a narrower proximal portion typically allows greater regrowth and healing of the neck of the femur towards the area of the greater trochanter, than generally occurs upon implantation of conventional IM nail heads.

For some applications, IM nail 30 comprises both narrower proximal portion 182 and locking mechanism 51, as described hereinabove. For other application, the IM nail comprises only one of these features, but is generally otherwise conventional.

Figure 6:
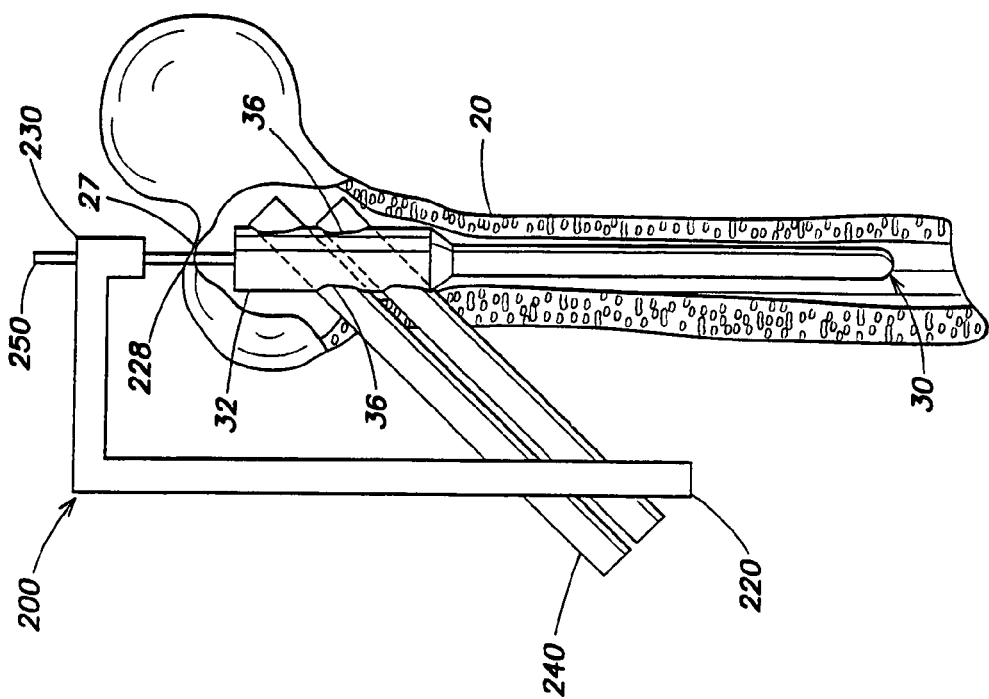
FIG. 6 is a schematic illustration of an IM locating tool, in accordance with an embodiment of the present invention.

FIG. 6 is a schematic illustration of an IM locating tool 200, in accordance with an embodiment of the present invention. In this embodiment, proximal portion 32 of IM nail 30 does not extend to surface region 27 of femur 20. Without the use of IM locating tool 200, it is sometimes difficult for the surgeon to locate proximal portion 32 of IM nail 30 if post-operative access to the implant becomes necessary. A distal end 220 of the locating tool comprises or is removably coupled to one or more connecting elements 240, which typically comprise a locking mechanism similar to locking mechanism 51, for locking to IM nail 30, as described hereinabove with reference to FIG. 3. Alternatively, connecting elements 240 comprise another locking mechanism, such as protrusions, clips, or pegs.

To use the locating tool, the surgeon temporarily couples connecting elements 240 to respective head holes 36 of IM nail 30. For some applications, the surgeon performs this coupling by removing any sleeves or screws present in holes 36, and inserting a sleeve (not shown), which may be similar to sleeve 50 described hereinabove with reference to FIG. 3, into each hole 36. The surgeon then couples each connecting element 240 to one of the sleeves. Alternatively, connecting elements 240 are directly coupled to head holes 36. In either case, after the connecting elements are in a fixed position with respect to IM nail 30, tool 200 is typically placed or slid onto the connecting elements, so as to assume a known, rigid position with respect thereto. (In embodiments in which connecting elements 240 are an integral part of tool 200, this step is not necessary.) The use of at least two connecting elements 240 provides for a known, fixed orientation of IM locating tool 200 with respect to IM nail 30. For applications that use only a single connecting element 240, means are provided for ensuring a fixed rotational angle between connecting element 240 and hole 36, thereby providing a known, fixed orientation of IM locating tool 200 with respect to IM nail 30. For example, such means may include a slot in hole 36.

Typically, coupling IM locating tool 200 to IM nail 30 automatically positions a proximal end 230 of the locating tool so as to indicate a site 228 of surface region 27 substantially directly over proximal portion 32 of the IM nail. The surgeon typically uses knowledge of the location of site 228 in order to determine an appropriate location at which to drill. For some applications, proximal end 230 comprises means for guiding a marking device 250 or drill, such as a hole through which the marking device or drill is inserted.

Figure 7:
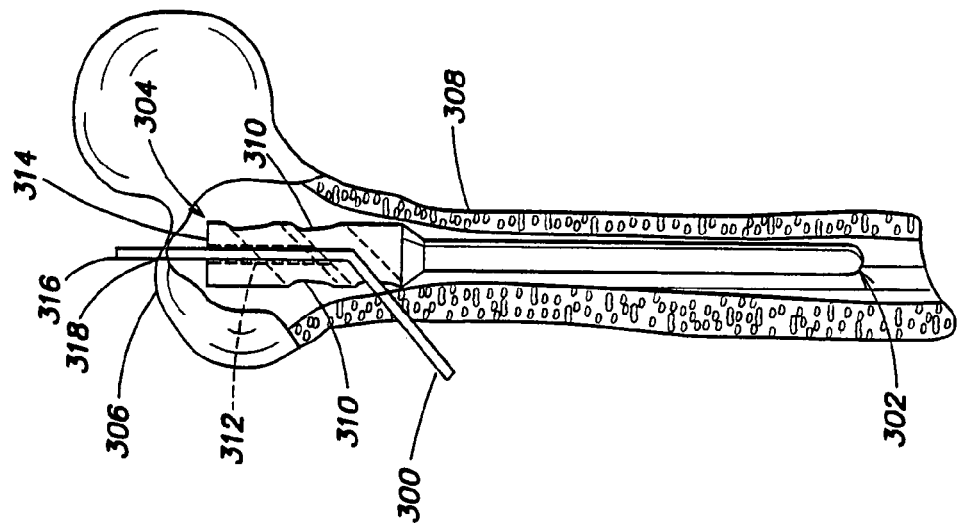
FIG. 7 is a schematic illustration of another IM locating tool, in accordance with an embodiment of the present invention.

FIG. 7 is a schematic illustration of an IM locating tool 300, in accordance with an embodiment of the present invention. An IM nail 302 comprises a proximal portion 304 which does not extend to a surface region 306 of a femur 308. The proximal portion defines one or more head holes 310, and a longitudinal channel 312 open to at least one of the head holes and to a proximal end 314 of proximal portion 304. Without the use of IM locating tool 300, it is sometimes difficult for the surgeon to locate proximal portion 304 of IM nail 302 if post-operative access to the implant becomes necessary.

IM locating tool 300 comprises an elongated element that is both bendable and resilient, i.e., is able to bend while maintaining longitudinal strength. A tip 316 of tool 300 is sufficiently sharp to pass through femur 308. In order to locate a site 318 of surface region 306 substantially directly over proximal portion 304 of the IM nail, the surgeon inserts tool 300, sharp end first, into one of head holes 310. The surgeon guides the tool through channel 312, so that the tool bends to conform with the channel. After pushing the tool so that tip 316 reaches the end of channel 312 at proximal end 314, the surgeon continues to push with sufficient force so that tip 316 punches through femur 308 and emerges from surface region 306 at site 318, thereby externally indicating the location of the site. Alternatively, tip 316 is threaded, and the surgeon rotates tool 300 so as to screw tip 316 through femur 308. Further alternatively, tool 300 comprises a flexible drill bit, and the surgeon drills the tool through femur 308. The surgeon typically uses knowledge of the location of site 318 attained through use of tool 300 in order to determine an appropriate location at which to drill during post-operative access to the IM nail.

Reference is now made to FIG. 8, which is a schematic illustration of an introducer 400 applied to a femur 402, in accordance with an embodiment of the present invention. Introducer 400 is adapted to actively reduce and align a fracture 404 of femur 402, such as a subtrochanteric fracture, while generally minimizing the required size of an incision in the vicinity of the fracture. Introducer 400 comprises a support 406, a coupling element 408, and a multi-axial control element, such as a biaxial control element 410. Coupling element 408 is adapted to couple introducer 400 to an IM nail 412, which is inserted into a medullary canal 414 of femur 402. For example, coupling element 408 may comprise a male element adapted to be inserted into a hole defined by a proximal end of a proximal head 416 of IM nail 412. Other coupling mechanisms used by conventional introducers may also be used. One or more neck screws 420 secure the IM nail at the head within a femoral head 422 of femur 402. Introducer 400 is typically shaped so as to define one or more holes (not shown) for guiding respective neck screws 420 during their insertion into femoral head 422.

Introducer 400 is shaped to facilitate use with a pin 424. During a procedure (which is generally performed using real-time imaging, such as fluoroscopy), pin 424 is inserted through femur 402 and through an elliptical or otherwise elongated hole 426, defined by a distal region 428 of IM nail 412 in a vicinity of fracture 404, such that the fracture is between the pin and coupling element 408. For some applications, pin 424 is threaded in a vicinity of a bone-penetrating tip 430 thereof and/or in a vicinity of one or both regions 432 thereof that pass through femur 402. Pin 424 typically has a diameter of between about 3 and about 6 mm, typically between about 4 and about 5 mm.

Figure 9A:
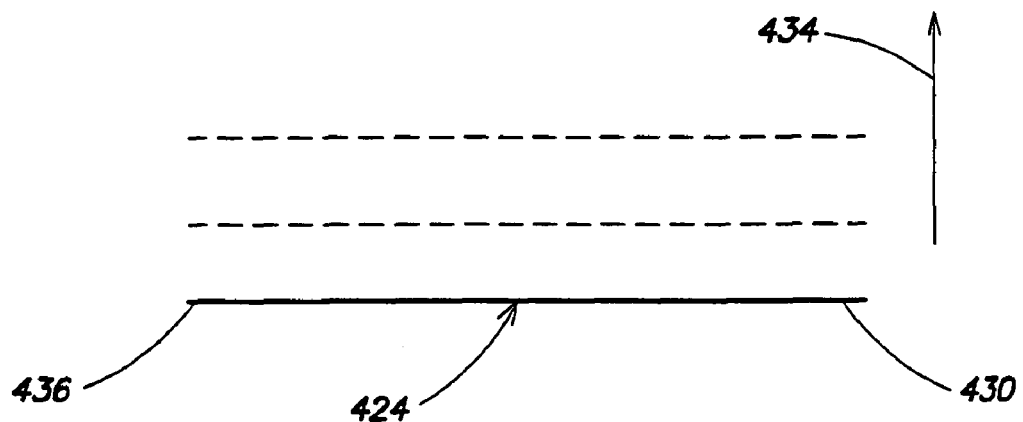
FIGS. 9A and 9B are schematic illustrations of motion of a pin of the introducer of FIG. 8, in accordance with an embodiment of the present invention.
Figure 9B:
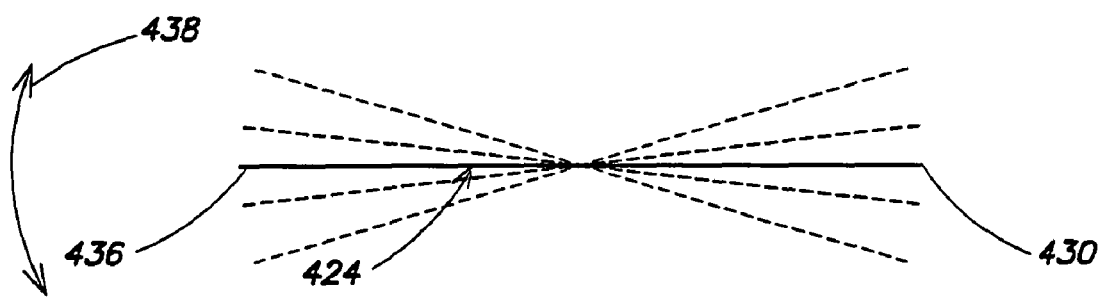

Reference is now made to FIGS. 9A and 9B, which are schematic illustrations of motion of pin 424, in accordance with an embodiment of the present invention. Biaxial control element 410 is adapted to move pin 424 along two axes, as follows:

translationally, for example, in a cephalad direction toward support 406 (i.e., in the direction generally indicated by arrow 434). In this manner, bone-penetrating tip 430 and a physician-manipulated end 436 of pin 424 generally move equal distances (FIG. 9A). Such cephalad movement serves to reduce fracture 404; and rotationally, such that bone-penetrating tip 430 and physician-manipulated end 436 move in opposite directions, i.e., tip 430 moves closer to or further away from support 406 in one of the directions generally indicated by arrow 438, while end 436 moves in the opposite direction (FIG. 9B). Such rotational movement serves to properly align fragments 440 and 442 of femur 402 with one another (FIG. 8).

Elongated hole 426 typically has a length of about 10 mm to about 12 mm. Pin 424 is typically inserted through elongated hole 426 near a distal end thereof, which allows substantial rotation and cephalad motion of the pin before the pin comes in contact with a proximal end of the hole, e.g., about 10 mm of motion. (FIG. 8 shows the pin already at the proximal end of hole 426.)

Reference is again made to FIG. 8. After fracture 404 has been reduced and aligned, a screw (not shown) is typically screwed through a hole 444, defined by distal region 428 of IM nail 412, into fragment 440, in order to fix IM nail 412 to fragment 440. Hole 444 is typically circular and positioned distally to elongated hole 426 (as shown), or proximal thereto (configuration not shown). Pin 424 is then removed from elongated hole 426. Optionally, a second screw (not shown) is screwed through elongated hole 426 into fragment 440 to further fix the IM nail to the fragment.

In an embodiment of the present invention, distal region 428 of IM nail 412 defines a secondary elliptical or otherwise elongated hole 446, in a distal vicinity of elongated hole 426. In this embodiment, after removal of pin 424 from elongated hole 426, the pin is inserted through secondary hole 446. Biaxial control element 410 further moves pin 424 in the cephalad direction towards support 406, in order to further reduce fracture 404. Typically, about 10 mm of reduction is performed using elongated hole 426, and up to about an additional 10 mm of reduction is performed using secondary elongated hole 446, for a total reduction of up to about 20 mm. It has been the inventor's experience that fractures rarely require reduction of more than about 20 mm, after initial reduction with a fracture table.

In an embodiment of the present invention, biaxial control element 410 comprises a first member such as a first leg 448, and a second member such as a second leg 450, the first and second members comprising set screws 452 and 454, respectively. The first and second legs each define one or more elliptical or otherwise elongated holes 456 and 458, respectively. When inserted into elongated hole 426 of IM nail 412, pin 424 passes through one of holes 456 and one of holes 458. The pin is initially positioned near respective distal ends of the holes. Tightening set screw 452 pushes the pin towards a proximal end of the one of the holes 456, while tightening set screw 454 pushes the pin towards a proximal end of the one of the holes 458. Therefore:

tightening both set screws to the same extent and substantially simultaneously moves pin 424 in the cephalad direction towards support 406;

tightening only set screw 452 rotates pin 424 clockwise, in order to align fragments 440 and 442; and tightening only set screw 454 rotates pin 424 counterclockwise, in order to align fragments 440 and 442.

Typically, a combination of such tightening motions is performed in order to reduce and align fracture 440. It is noted that for some configurations (such as that shown in FIG. 8), tightening one of the set screws also induces some net cephalad motion of the center of pin 424. For some applications, one or both of legs 448 or 450 are removably coupled to support 406 by coupling elements 460 or 462, respectively (e.g., comprising screws or clips). For example, leg 450 may be removably coupled to support 406, in which case leg 448 and support 406 are used to insert IM nail 412 into intramedullary canal 414. The absence of leg 450 during this insertion generally makes introducer 400 easier to manipulate. After insertion of the IM nail, leg 450 is coupled to support 406.

In an embodiment, biaxial control element 410 comprises an optional shaped element, such as shaped element 454, coupled within biaxial control element 410 so as to provide means for pulling pin 424 (or otherwise inducing motion of pin 424) in the caudal direction. Shaped element 454 is coupled via a joint 456 to the proximal tip of set screw 452. (Alternatively or additionally, a shaped element is coupled to set screw 454.) Pin 424 passes through a hole in shaped element 454, such that joint 456 allows set screw 452 to rotate while shaped element 454 substantially does not rotate. In addition, joint 456 couples shaped element 454 and set screw 452 such that movement of either one along the proximal/distal axis induces movement of the other one in the same direction. In particular, distal (caudal) motion of set screw 452 causes corresponding caudal motion of pin 424. (By contrast, in embodiments not having shaped element 454 or equivalents thereof, proximal motion of set screw 452 causes cephalad motion of pin 452, while distal motion of set screw 452 does not induce any substantial motion of pin 452.) It is noted that the configuration and shape of shaped element 454 shown in FIG. 8 is by way of illustration and not limitation. A person of ordinary skill in the art of mechanical design, having read the disclosure of the present patent application, would be able to develop other substantially equivalent means for providing cephalad and caudal motion of pin 424.

In an embodiment of the present invention, introducer 400 is used in conjunction with a surgical plate having one or more elliptical or otherwise elongated holes through which pin 424 is inserted (configuration not shown). The plate is secured to the outside of femur 402 in a position suitable for reducing fracture 404 and for aligning fragments 440 and 442. For this embodiment, techniques described hereinabove with reference to FIGS. 8, 9A, and 9B are adapted to for use with the surgical plate, mutatis mutandis.

Figures 10, 11:
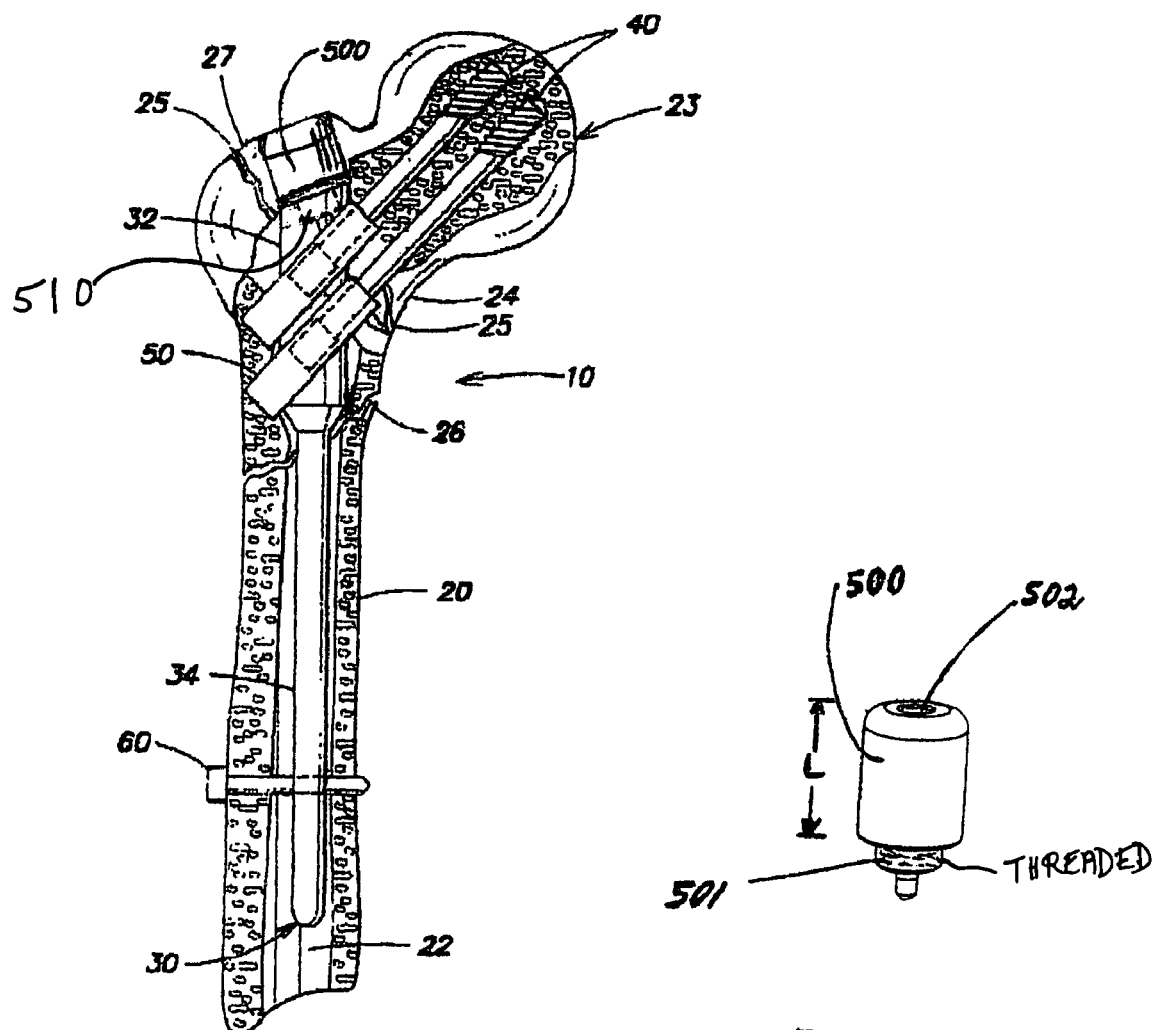
FIG. 10 is a schematic illustration similar to FIG. 1, but showing an elongated device at the top of the elongated member 32.
FIG. 11 shows details of the elongation device shown in FIG. 10.

FIGS. 10 and 11 show an embodiment of a nail elongation device 500. The need for such an elongation device is as follows. After the elongated member 32 (nail) and screws 40 are inserted, intra-operative x-ray control may demonstrate that too much fracture impaction may occur (because of the nature of the particular fracture being repaired. The surgeon may then use the nail elongation device 500, which comes in different lengths L in FIG. 11 to modify the proximal length of the nail 32. The elongation device 500 has at its upper end an arrangement such as a screwdriver slot or an Allen wrench opening 502 to receive an insertion/removal device (such as a screw driver or Allen wrench). The device 500 will then be threadedly connected to the upper part of the nail 32 using the arrangement 501 (such as a thread located at its lower end) which will be threaded into a threaded opening 510 at the top of nail 32. The reason for using a fracture fixation device, which is entirely inserted in the bone, is to facilitate fracture impaction. Fracture impaction is very important for fracture healing. However, sometimes excessive fracture motion may occur in such a situation. In order to control the amount of fracture impaction and not to get too excessive fracture motion (and hence to result in fracture instability) the nail elongation device 500 will be used. Many times the judgment of what is the best treatment for a given fracture can be done only intra-operative (i.e., during the procedure) and hence the importance of the nail elongation device 500 of the present invention.

If, during the operation to repair the fracture, the surgeon determines that the upper portion of the elongated member 32 should be raised so as to be in, for example, the position shown by the elongation member 500 in FIG. 10, the surgeon will then select an elongation member 500 of appropriate length L to be screwed into the threaded receptacle 510 at the upper end of elongated member 32 so that the elongation member 500 is in the desired position relative to the upper end of the bone. In FIG. 10, the elongation member 500 is shown with its upper surface substantially at the same level as the upper end of the femur bone being repaired. In other instances, other length elongation members 500 can be used, depending upon the situation at the time of the surgery, to achieve the desired result. As indicated above, the elongated members are made in varying lengths L for selection by the surgeon during the operation, in order to control the amount of fracture impaction in the particular fracture being repaired.

Figure 11A:
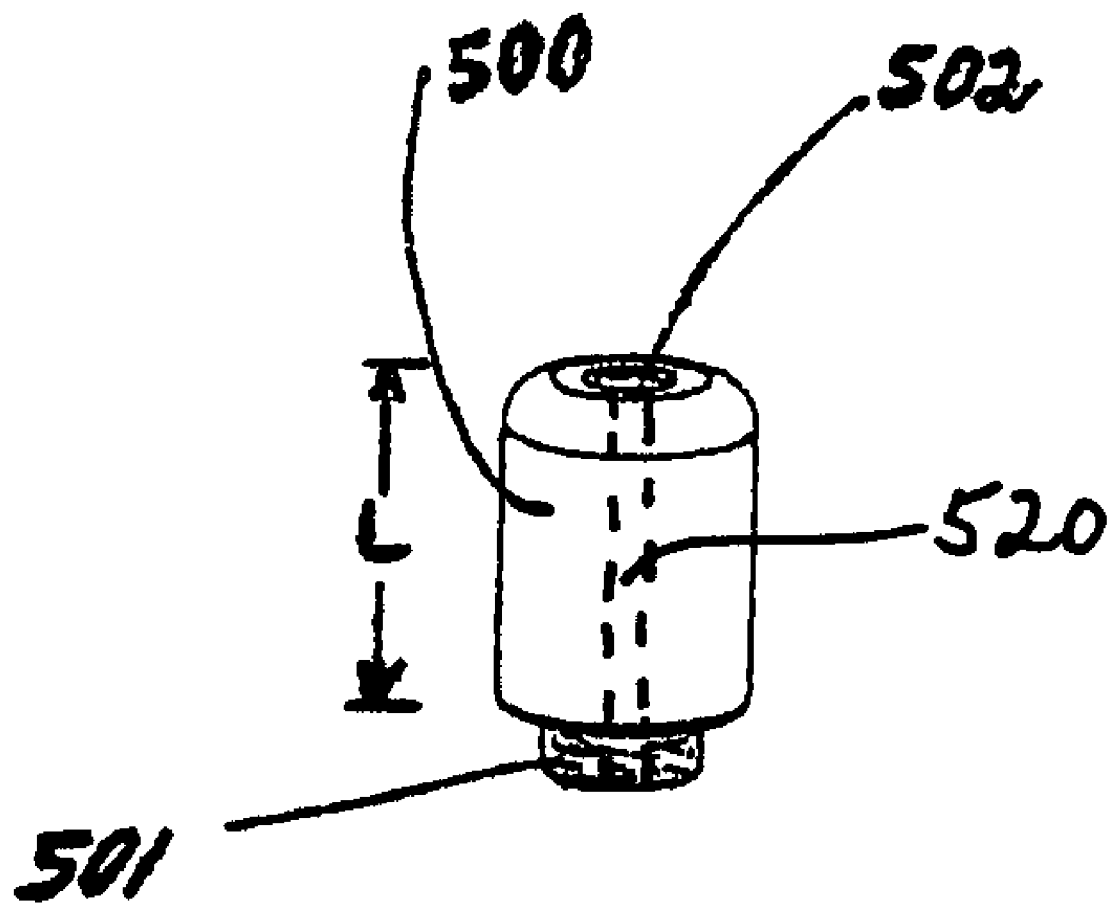
FIG. 11A shows a modified elongation device.

As shown in FIG. 11A, the elongation member 500 may have an internal hollow bore 520 therein, which extends therethrough in the longitudinal direction. This bore 520 is for receiving an elongated member such as member 300, during the procedure illustrated in FIG. 7 and described hereinabove. This procedure is carried out for locating the elongated member when bone, for example, has grown over the upper end thereof.

Figure 12:
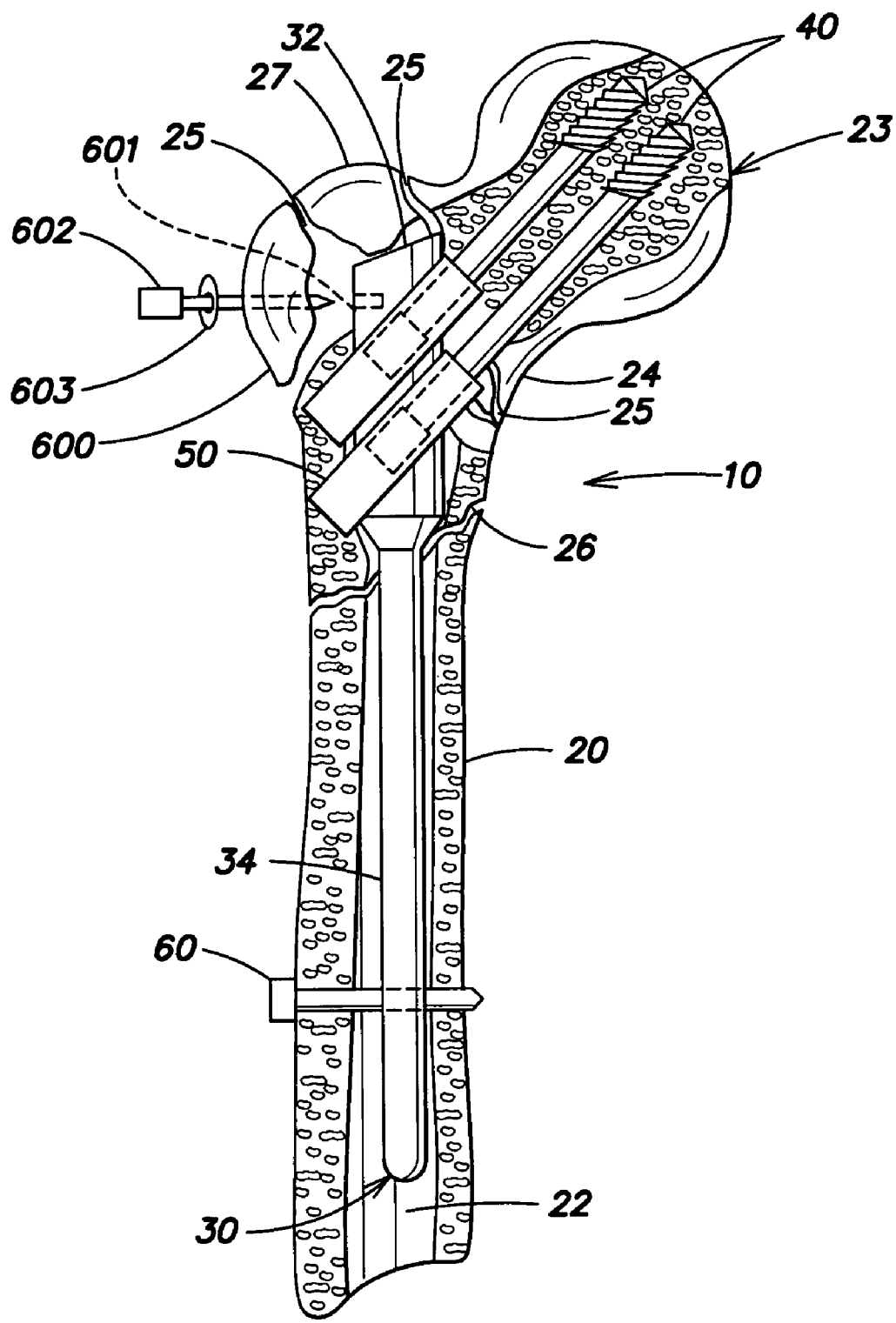
FIG. 12 shows the system of FIG. 1 with an attachable member for retaining in position a broken lateral wall of an upper femur.
Figure 13:
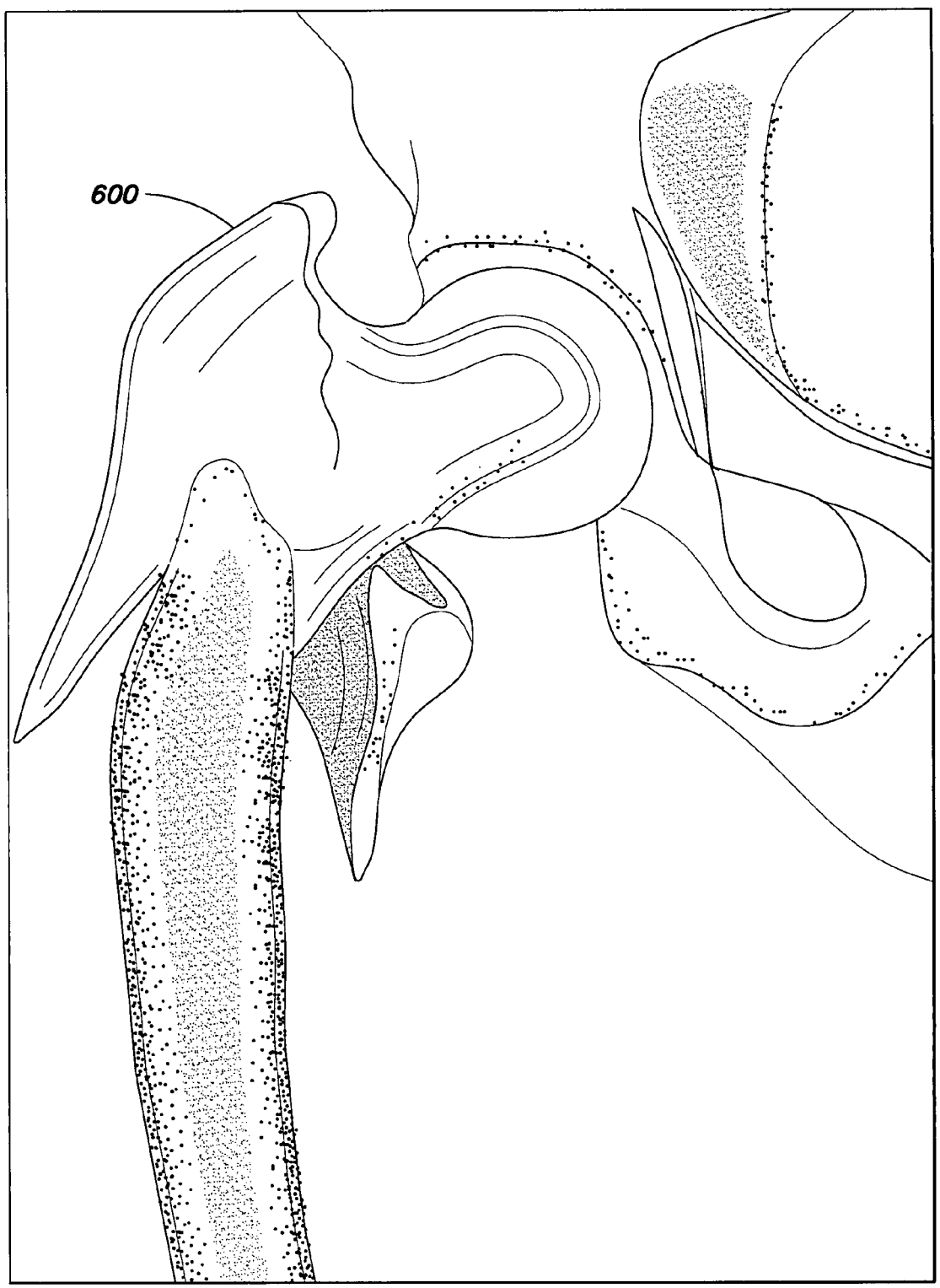
FIGS. 13-15 show X-ray pictures of the repair of a fracture of the femur.
Figure 14:
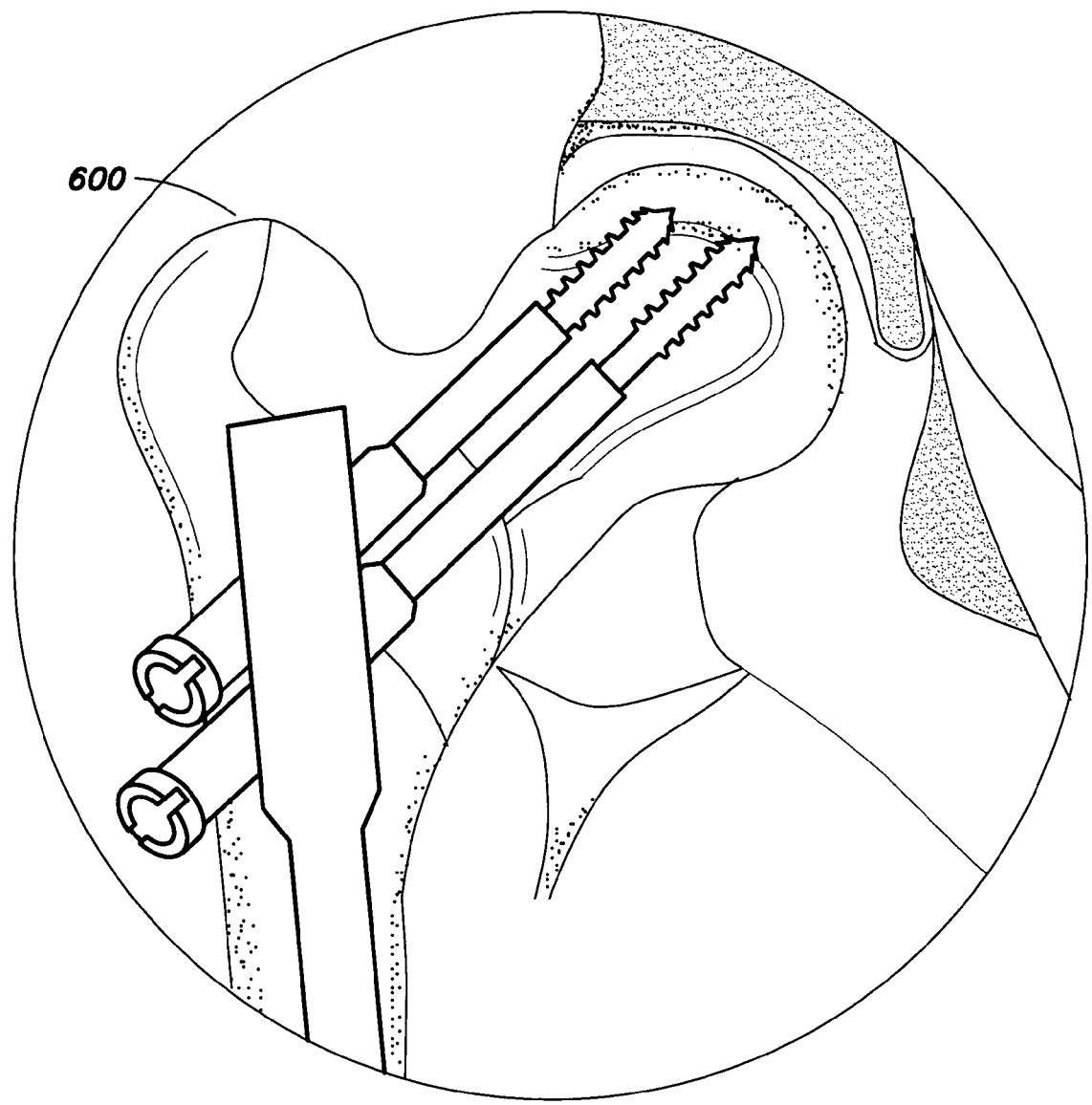
Figure 15:
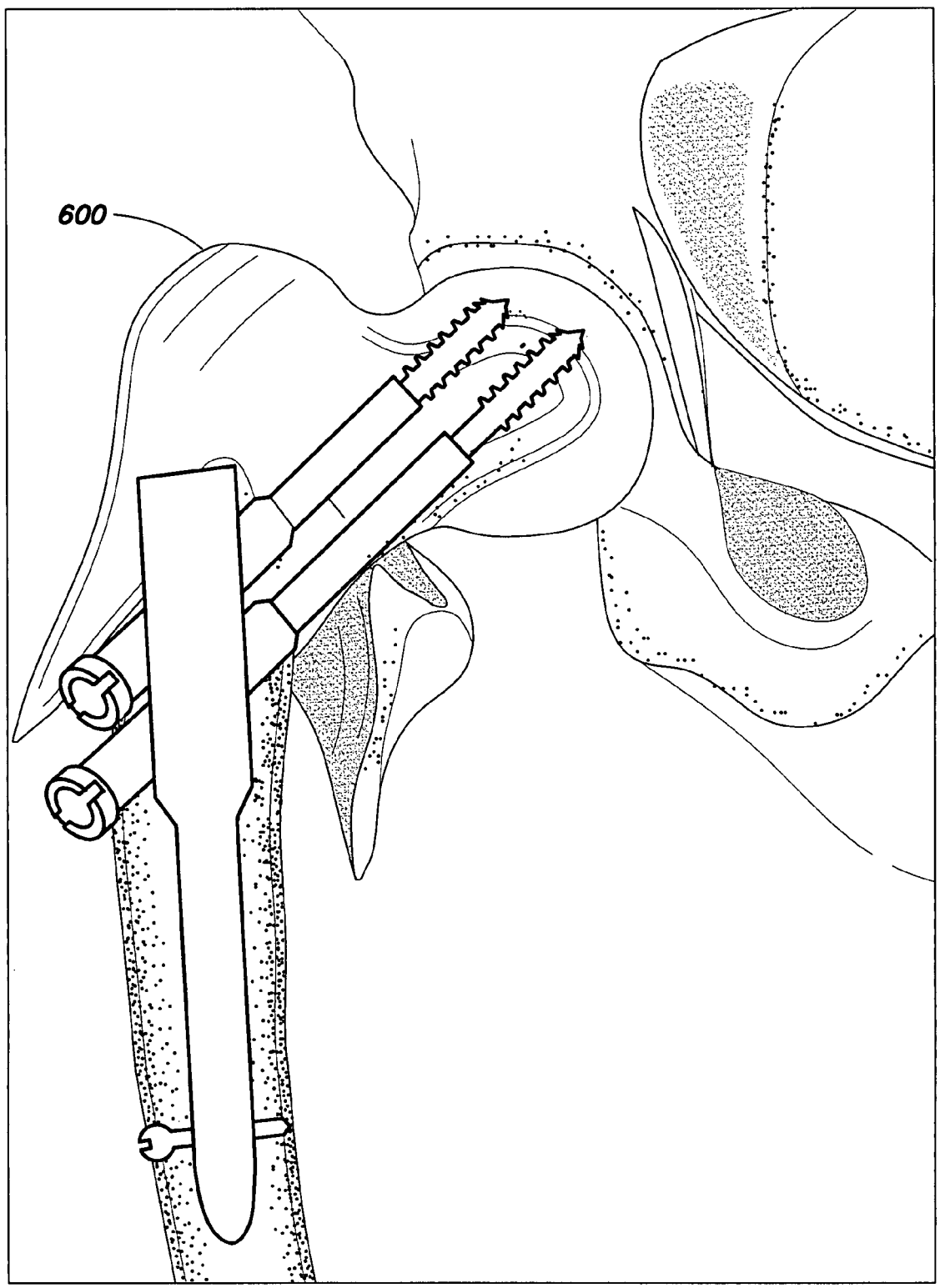

Some hip fractures are also broken at their upper lateral part which is called the lateral wall (600 in FIG. 12). FIGS. 13-15 show x-rays of a serious hip fracture. The pre-operative picture, FIG. 13, shows a hip fracture in which the lateral wall 600 is also broken. In FIG. 14, the intra operative picture, it is seen that the fracture was reduced and fixed very nicely using the arrangement shown, for example, in FIG. 1. Unfortunately, as seen in the post operative picture, FIG. 15, the lateral wall 600 lost contact and moved aside. This problem is solved by the structure shown in FIG. 12.

As shown in FIG. 12, in order to more positively secure the broken lateral wall of the upper femur 600, the proximal part of the elongated member (nail 32) is provided with an opening (bore) 601, such as threaded hole or bore, arranged to accept a fixation member such as a threaded screw or pin with or without an auxiliary part 603 such, for example, a washer or a mini plate. The broken lateral wall 600 can be secured to its anatomical place using the structure shown in FIG. 12. The broken lateral wall 600 is positively retained in position during the healing stage to prevent the result shown in FIG. 15.

Figure 16C:
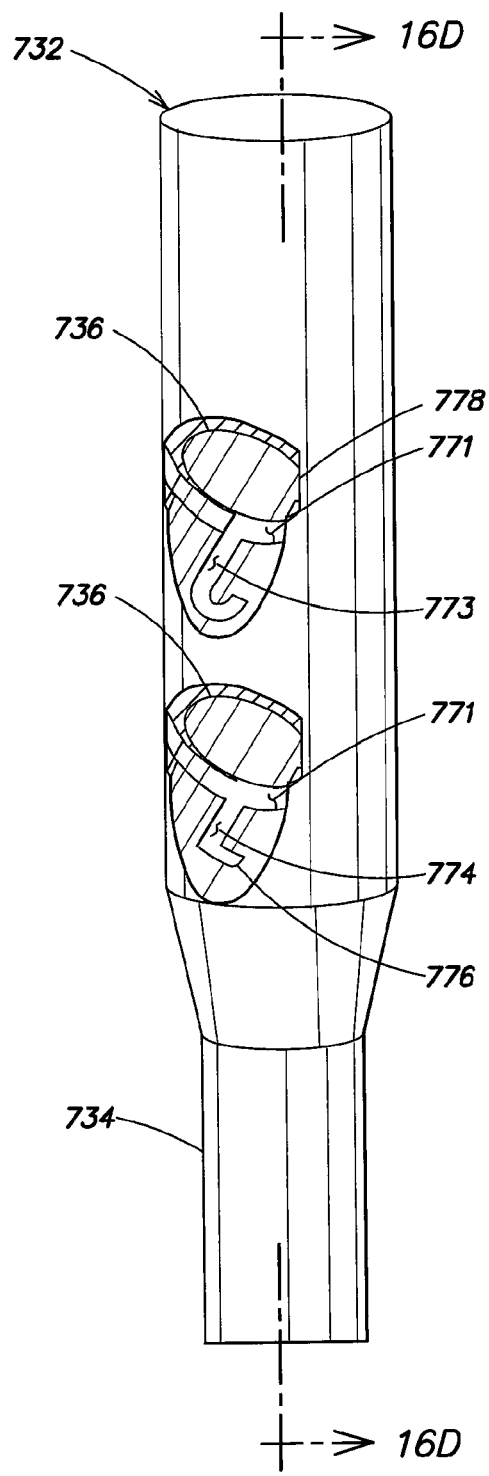
FIG. 16C is a schematic illustration of the head of the IM nail of FIG. 1.
Figure 16D:
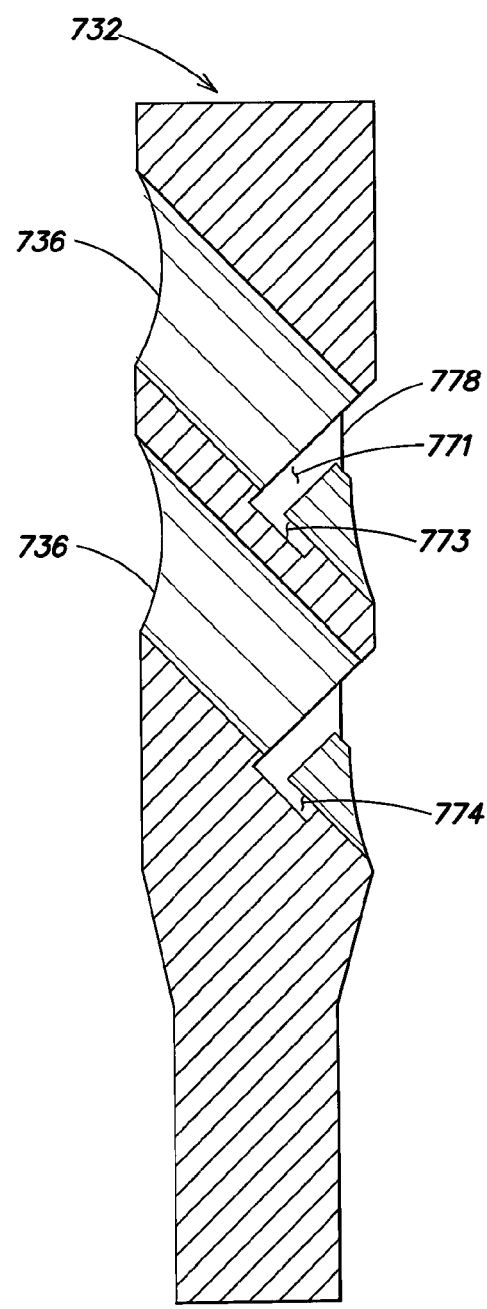
FIG. 16D is a cross-sectional illustration of the head through the line A-A of FIG. 16C, in accordance with another embodiment of the present invention.
Figure 16E:
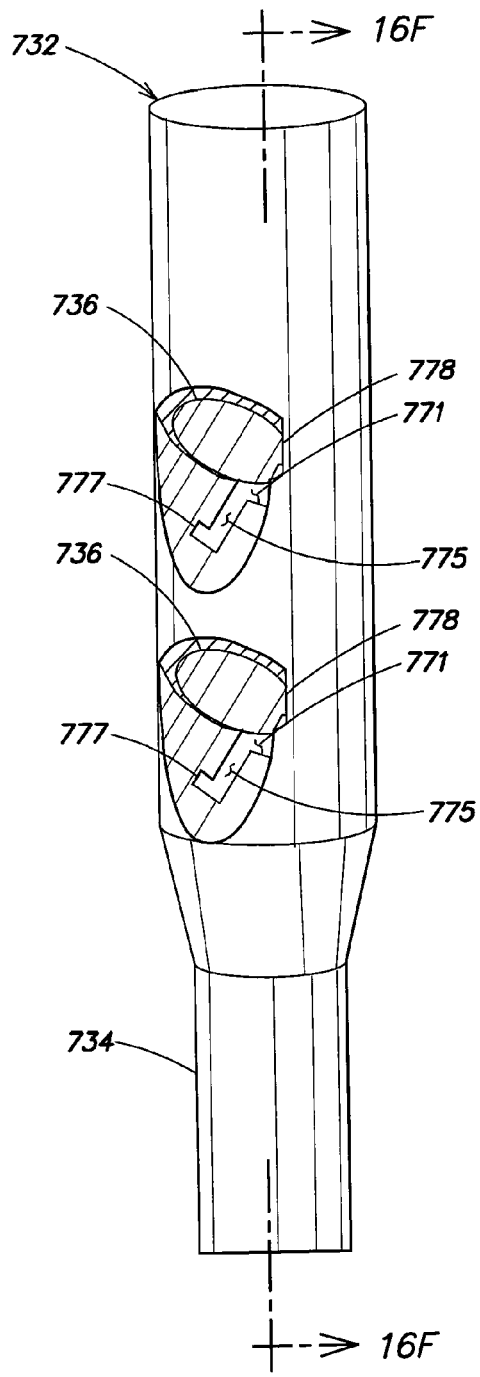
FIG. 16E is a schematic illustration of the head of the IM nail of FIG. 1.
Figure 16F:
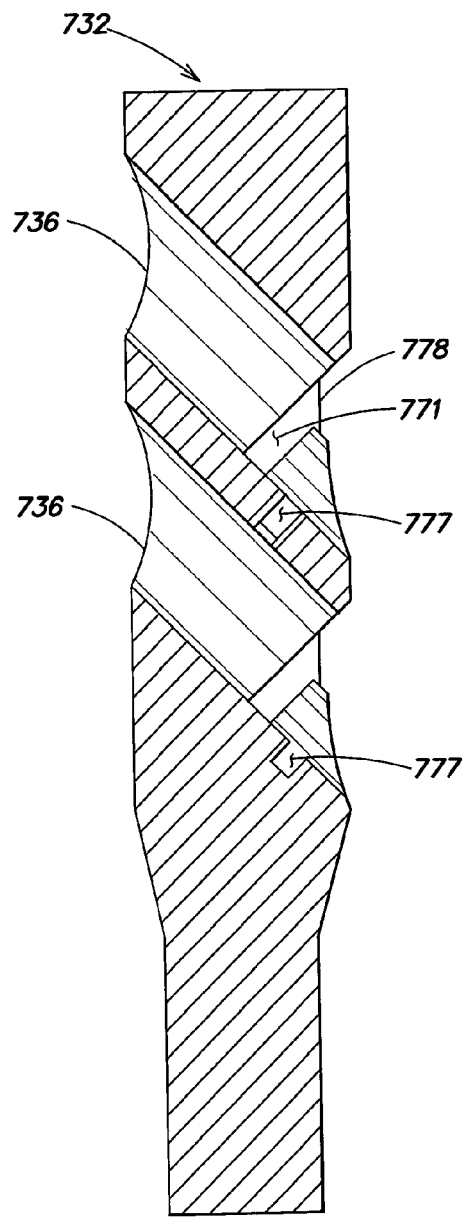
FIG. 16F is a cross-sectional illustration of the head through the line A-A of FIG. 16E, in accordance with another embodiment of the present invention.

Reference is now made to FIGS. 16A-16F. FIGS. 16A, 16C, and 16E are schematic illustrations of a head 732 of IM nail 734, and FIGS. 16B, 16D, and 16F are cross-sectional illustrations of head 732 through the line A-A of FIGS. 16A, 16C, and 16E, respectively, in accordance with respective embodiments of the present invention. In the embodiments shown in FIGS. 16A-16F, head 732 defines at least one hole 736, typically two holes 736, as shown. Holes 736 are typically oriented in an angled direction toward femoral head 23 (see FIG. 1) relative to a longitudinal axis of IM nail 734.

Figure 17:
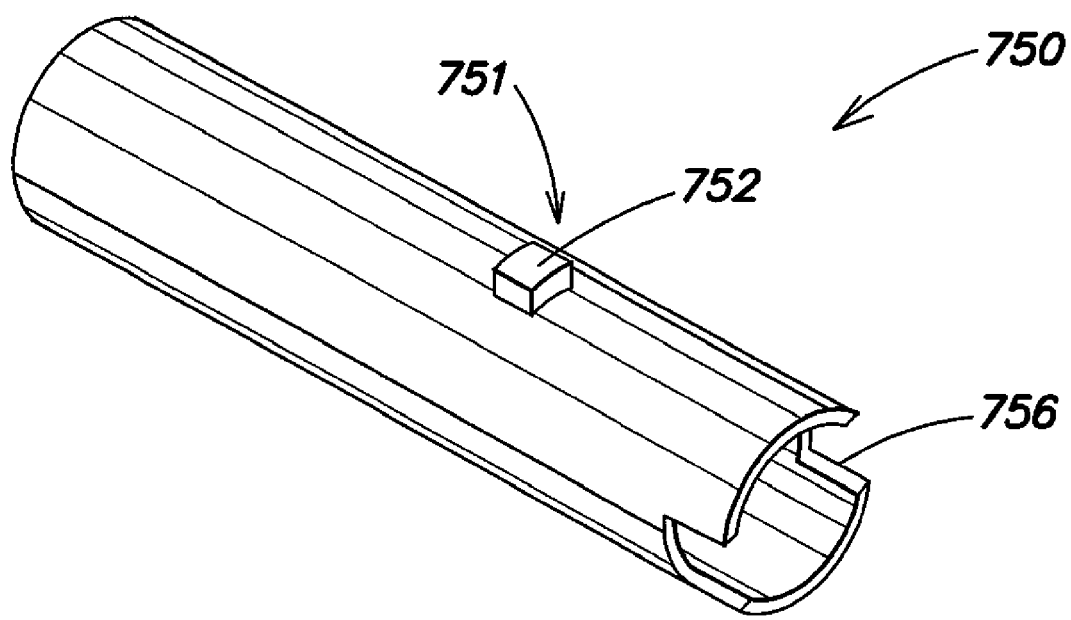
FIG. 17 is a schematic illustration of a sleeve for use with the IM system of FIGS. 1 and 16A-16F, in accordance with an embodiment of the present invention.

FIG. 17 is a schematic illustration of a substantially tubular sleeve 750 in accordance with an embodiment of the present invention, for possible use with the IM nails 734 shown in FIGS. 16A-16F or for other embodiments described herein. Sleeve 750 comprises an engagement mechanism 751, which engages head hole 736 (FIGS. 16A-16F), restricting rotational and longitudinal movement between sleeve 750 and head hole 736 (or more generally, the IM nail 734) after sleeve 750 is inserted into the head hole 736 of the IM nail 734. The engagement mechanism 751 typically comprises a male coupling element, such as a tab or projection 752 fixed or otherwise attached to, or formed integral with, the outer surface of sleeve 750. The tab or projection 752 is formed on a non-depressible portion of the sleeve 750.

In use, the sleeve 750 is inserted into head hole 736 and rotated until tab or projection 752 engages a female coupling element, such as a groove 771 of hole 736, entering the groove 771 through an entrance 778. (Alternatively, the male and female coupling elements can be reversed, i.e., the male coupling element provided on the IM nail 734 and the female coupling element provided on the sleeve 750.) Sleeve 750 is typically shaped to define at least one cutout 756 to receive a screwdriver used by the surgeon to align the tab or projection 752 with groove 771 (see FIG. 17). Groove 771 may be formed along or alongside the periphery or circumference of the head hole 736 (see FIG. 16B).

After tab or projection 752 has been inserted through entrance 778 into groove 771, sleeve 750 is rotated in an inferior-medial direction, causing the tab or projection to move in the groove 771 until tab or projection 752 reaches an upper endpoint of a slot 772 (FIG. 16A) or of a slot 773 or 774 (FIG. 16C) or of a slot 775 (FIG. 16E), all of which communicate with an end of the groove 771 opposite the entrance 778. The sleeve 750 is then moved longitudinally causing the tab or projection 752 to move or slide into the slot 772, 773, 774, 775, 776, 777.

For some applications, the slot through which tab or projection 752 slides is generally straight (e.g., slot 772 of FIG. 16A). Alternatively, the slot is curved (e.g., slot 773 of FIG. 16C) or has a sharp angle (e.g., slots 774 and 776 of FIG. 16C and slots 775 and 777 of FIG. 16E), for example in order to reduce any possibility that the sleeve 750 may become loosened during screwing of screw 40 into femoral head 23 (FIG. 1). Other variations in the shape of the slot into which the tab or projection 752 is moved or slid during the implantation procedure are also envisioned including combinations of the disclosed shapes.

The shape of the slot, or more generally the female coupling element, is designed to restrict rotational and longitudinal movement of the sleeve 750 relative to the IM nail 734, and in some cases, to inhibit or prevent rotational and/or longitudinal movement of the sleeve 750 relative to the IM nail 734.

Typically, but not necessarily, engagement mechanism 751 inhibits longitudinal movement of sleeve 750 with respect to head hole 736 in one, most important direction, i.e., downward motion of the sleeve 750, thereby preventing sliding of the sleeve 750 out of the head hole 736 once the nail 734 and screws 40 are subjected to body load of the subject. Longitudinal movement in the opposite direction i.e., upward, is restricted by the upward direction of head hole 736. For example, with reference to the embodiment shown in FIGS. 16A and 16B, once the tab or projection 752 is at the bottom or end of the slot 772, further downward movement of the sleeve 750 relative to the IM nail 734 is prevented (by contact between the tab or projection 752 and the wall of the IM nail 734 defining the slot 772). However, upward movement of the sleeve 750 relative to the IM nail 734 is restricted, i.e., permitted only a limited extent, since the tab or projection 752 can move upward in the slot 772 until it contacts the wall of the groove 771.

Additionally, mechanism 751 allows rotational movement of sleeve 750 with respect to the head hole 736 in at least one direction during insertion in groove 771. Further engagement of engagement mechanism 751 in slot 772 (or 773 or 774, 776 or 775, 777) will inhibit rotational movement of sleeve 750 with respect to head hole 736. This can be provided in some embodiment by dimensioning the width of the slot 772, 773, 774, 775, 776, 777 to be equal to or only marginally larger than the width of the tab or projection 752.

IM nail 734 can be formed such that the movement restrictions provided by the cooperation of the male coupling element, e.g., tab or projection 752, and the female coupling element, i.e., groove 771 and slot 772, 773, 774, 775, is a total restriction unless subjected to releasing maneuvers. The engagement mechanism can, in one embodiment, be configured to be released only by rotational and longitudinal disengagement maneuvers. Alternatively, the engagement mechanism can be configured to provide engagement of the sleeve 750 with the head hole 736 such that a longitudinal movement is achievable, following the engagement, only after rotating the sleeve 750.

In sum, selection of an appropriate shape of the slot in the IM nail 734 can allow for a total restriction or prevention of rotational movement of the sleeve relative to the IM nail 734 while allowing for limited longitudinal movement in only one direction (which arises in part from the initial positioning of the tab or projection 752 at the bottom or end of the slot). Other forms of the slot can require rotational movement of the sleeve relative to the IM nail 734 in order to allow for limited longitudinal movement in only one direction. The absence of such rotational movement will thus inhibit or prevent any longitudinal movement of the sleeve 750 relative to the IM nail 734. Selection of which shape slot to use can depend, for example, on the type of fracture, the bone which is fractured and the orientation of the IM nail and sleeve.

It will be appreciated that although some embodiments of the present invention have been shown and described herein for use in a femur, these embodiments may be adapted for use in other long bones of the extremities, such as the tibia and humerus, as would be evident to one skilled in the art. It will also be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for treating a fracture of a bone of a subject, comprising:
   an intramedullary (IM) elongate member insertable into a medullary canal of a first part of the bone and comprising a proximal head defining at least one hole therethrough;
   a sleeve comprising an engagement mechanism arranged to engage one of the at least one hole when the sleeve is within the hole, such engagement restricting rotational and longitudinal movement between the sleeve and the proximal head of the elongate member after the sleeve is engaged with the at least one hole; and
   at least one screw or pin arranged inside the sleeve for securing a second part of the bone to the first part of the bone,
   the engagement mechanism including a male coupling element arranged to engage with a female coupling element on the elongate member such that longitudinal movement of the sleeve relative to the elongate member while the male coupling element is engaged with the female coupling element is possible only after rotation of the sleeve relative to the elongate member while the male coupling element is engaged with the female coupling element,
   the female coupling element being located on the surface around each of the at least one hole and each female coupling element comprising:
   a first portion that allows, while the male coupling element is situated in the first portion, rotation of the sleeve relative to the elongate member from an entrance to the first portion to an end of the first portion after which further rotation of the sleeve relative to the elongate member is prevented; and
   a second portion beginning at the end of the first portion and that, while the male coupling element is situated in the second portion, allows longitudinal movement of the sleeve relative to the elongate member and prevents rotation of the sleeve relative to the elongate member.

2. Apparatus according to claim 1, wherein said elongate member is a nail.

3. Apparatus according to claim 1, wherein the male coupling element of the engagement mechanism comprises a tab or projection that protrudes from an outer surface of the sleeve.

4. Apparatus according to claim 3, wherein the proximal head defines each female coupling element located on the surface around the at least one hole, the tab or projection being arranged to engage the female coupling element so as to restrict rotational and longitudinal movement between the sleeve and the proximal head.

5. Apparatus according to claim 1, wherein the proximal head defines each female coupling element located on the surface around the at least one hole.

6. Apparatus according to claim 5, wherein the first portion of the female coupling element is part of a groove in the proximal head.

7. Apparatus according to claim 6, wherein the second portion of the female coupling element is part of a slot having one end communicating with the groove.

8. Apparatus according to claim 7, wherein the slot is straight.

9. Apparatus according to claim 7, wherein the slot is curved.

10. Apparatus according to claim 7, wherein the slot has a sharp angle.

11. Apparatus according to claim 5, wherein the female coupling element is arranged to inhibit rotational movement of the sleeve relative to the proximal head.

12. Apparatus according to claim 1, wherein the engagement mechanism is formed on a nondepressible portion of the sleeve.

13. Apparatus according to claim 1, wherein the elongate member is formed such that the restriction is a total restriction unless subjected to releasing maneuvers.

14. Apparatus according to claim 13, wherein the engagement mechanism is arranged to be released only by rotational and longitudinal disengagement maneuvers.

15. Apparatus according to claim 13, wherein the second portion is arranged to allow restricted longitudinal movement of the sleeve relative to the elongate member.

16. A method for treating a fracture of a bone of a subject, comprising
    inserting an intramedullary (IM) elongated member into a medullary canal of a first part of the bone;
    engaging a sleeve with the elongate member;
    constructing the sleeve and elongate member such that the engagement of the sleeve with the elongate member restricts rotational and longitudinal movement between the sleeve and the elongate member, the step of constructing the sleeve and the elongate member comprising:
        providing the elongate member with a female coupling element; and
        providing the sleeve with a male coupling element arranged to engage with the female coupling element on the elongate member; and
    positioning a screw or pin inside the sleeve to thereby secure a second part of the bone to the first part of the bone,
the step of engaging the sleeve with the elongate member comprising:
    engaging the male coupling element with the female coupling element; and
    then while the male coupling element is engaged with the female coupling element,
        rotating the sleeve relative to the elongate member; and only then
        moving the sleeve longitudinally relative to the elongate member such that the longitudinal movement of the sleeve relative to the elongate member while the male coupling element is engaged with the female coupling element is possible only after rotation of the sleeve relative to the elongate member while the male coupling element is engaged with the female coupling element.

\* \* \* \* \*